United States Patent
Adhikarath Balan et al.

(10) Patent No.: US 12,310,596 B2
(45) Date of Patent: May 27, 2025

(54) INTERFACE MECHANISM FOR REPOSITIONING AND DEPLOYMENT OF OVER THE SCOPE CLIP

(71) Applicants: BOSTON SCIENTIFIC MEDICAL DEVICE LIMITED, Galway (IE); BOSTON SCIENTIFIC SCIMED, INC., Maple Grove, MN (US)

(72) Inventors: Arun Adhikarath Balan, Aluva (IN); Rajivkumar Singh, Thane (IN); Deepak Kumar Sharma, Muzaffarnagar (IN); Paul Smith, Smithfield, RI (US); Junaid Mohammed Shaikh, Surat (IN)

(73) Assignees: Boston Scientific Medical Device Limited, Galway (IE); Boston Scientific Scimed, Inc., Maple Grove, MN (US)

( * ) Notice: Subject to any disclaimer, the term of this patent is extended or adjusted under 35 U.S.C. 154(b) by 327 days.

(21) Appl. No.: 17/815,816

(22) Filed: Jul. 28, 2022

(65) Prior Publication Data
US 2023/0055904 A1   Feb. 23, 2023

Related U.S. Application Data

(60) Provisional application No. 63/260,412, filed on Aug. 19, 2021.

(51) Int. Cl.
*A61B 17/122* (2006.01)
*A61B 17/08* (2006.01)
*A61B 90/00* (2016.01)

(52) U.S. Cl.
CPC .......... *A61B 17/122* (2013.01); *A61B 17/083* (2013.01); *A61B 90/03* (2016.02)

(58) Field of Classification Search
CPC ..... A61B 17/122; A61B 17/083; A61B 90/03; A61B 2017/00296
See application file for complete search history.

(56) References Cited

U.S. PATENT DOCUMENTS

| 4,325,376 A | 4/1982 | Klieman et al. |
| 4,509,518 A | 4/1985 | McGarry et al. |

(Continued)

FOREIGN PATENT DOCUMENTS

EP   2 158 854   3/2010

*Primary Examiner* — Tan-Uyen T Ho
*Assistant Examiner* — Cherie M Poland
(74) *Attorney, Agent, or Firm* — Fay Kaplun & Marcin, LLP

(57) ABSTRACT

A system for treating tissue includes a cap mounted over a distal end of an endoscope, a clip mountable over the cap and including first and second jaws movably connected to one another between an insertion configuration, in which the first and second jaws extend over the cap to receive a target tissue therebetween, a review configuration, in which at least a portion of the clip extends into a field of view of the optical system of an endoscope, and a deployed configuration in which the clip is moved distally off of the cap so that the first and second jaws are drawn toward one another. A control element is configured so that movement proximally through the cap via a first distance moves the clip from the insertion configuration to the review configuration and a second distance moves the clip from the review configuration to the deployed configuration.

11 Claims, 11 Drawing Sheets

(56) References Cited

U.S. PATENT DOCUMENTS

| | | | |
|---|---|---|---|
| 5,104,395 | A | 4/1992 | Thornton et al. |
| 5,700,270 | A | 12/1997 | Peyser et al. |
| 8,430,892 | B2 | 4/2013 | Bindra et al. |
| 8,465,502 | B2 | 6/2013 | Zergiebel |
| 8,506,580 | B2 | 8/2013 | Zergiebel et al. |
| 9,186,136 | B2 | 11/2015 | Malkowski et al. |
| 9,408,610 | B2 | 8/2016 | Hartoumbekis |
| 9,526,501 | B2 | 12/2016 | Malkowski |
| 9,750,500 | B2 | 9/2017 | Malkowski |
| 9,775,624 | B2 | 10/2017 | Rockronhr et al. |
| 10,390,830 | B2 | 8/2019 | Schulz |
| 10,806,463 | B2 | 10/2020 | Hartoumbekis |
| 10,869,668 | B2 | 12/2020 | Privitera et al. |
| 2013/0296892 | A1* | 11/2013 | Sorrentino ........... A61B 17/072 606/143 |
| 2014/0228864 | A1* | 8/2014 | Jugenheimer ........ A61B 17/122 606/157 |
| 2020/0397445 | A1 | 12/2020 | Shikhman et al. |
| 2021/0052141 | A1 | 2/2021 | Schurr et al. |
| 2023/0027249 | A1* | 1/2023 | Adhikarath Balan ....................... A61B 1/00137 |

\* cited by examiner

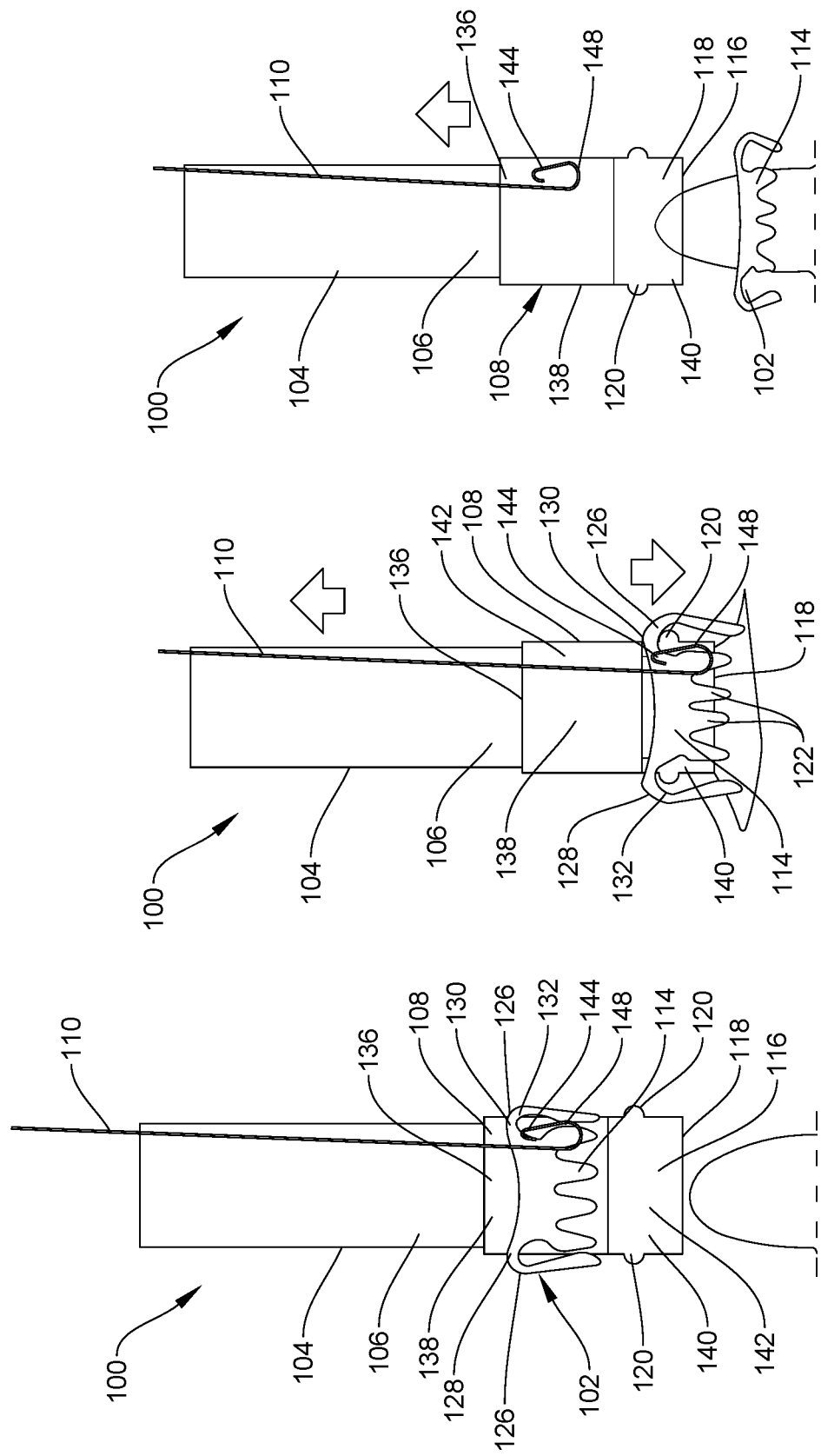

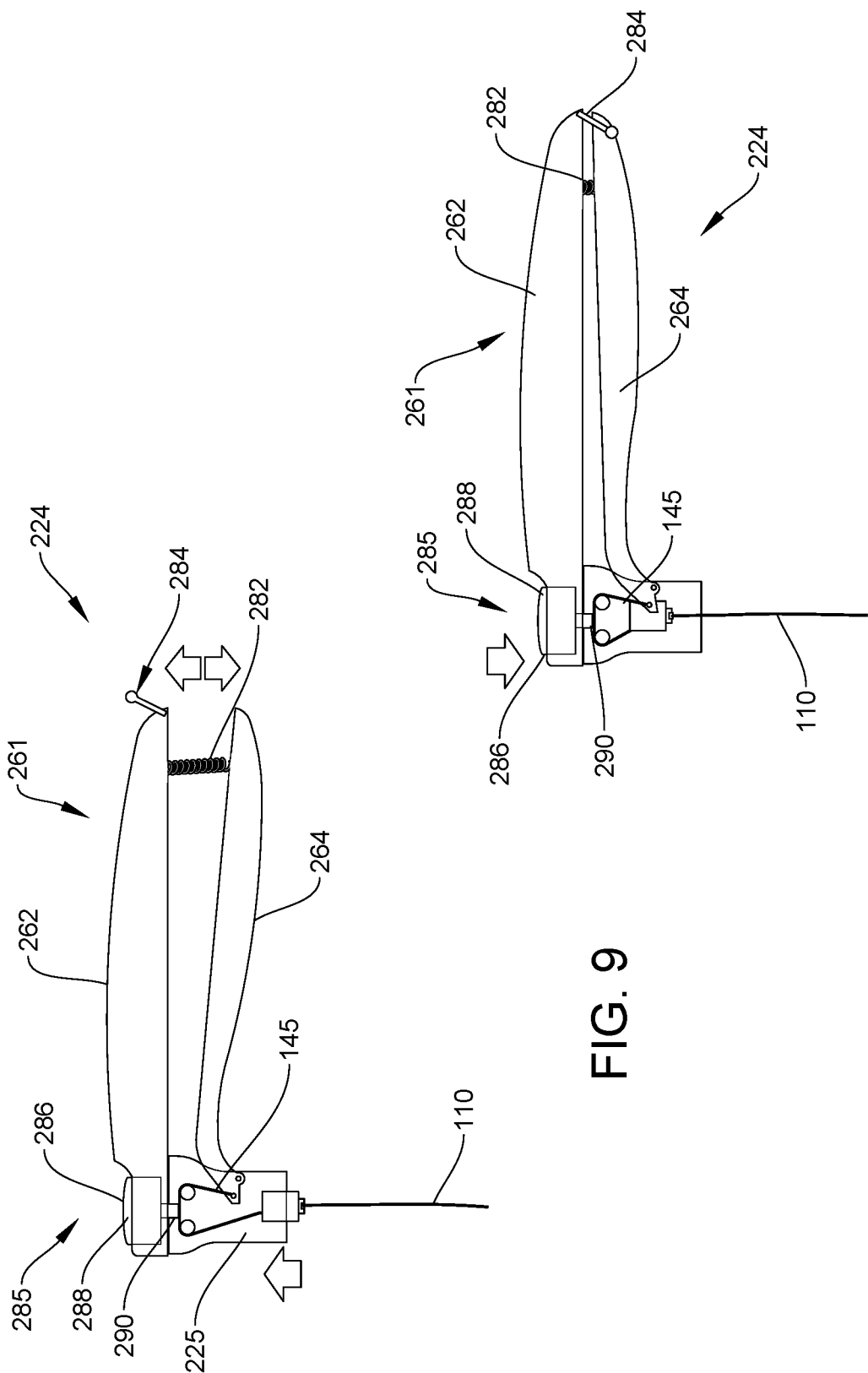

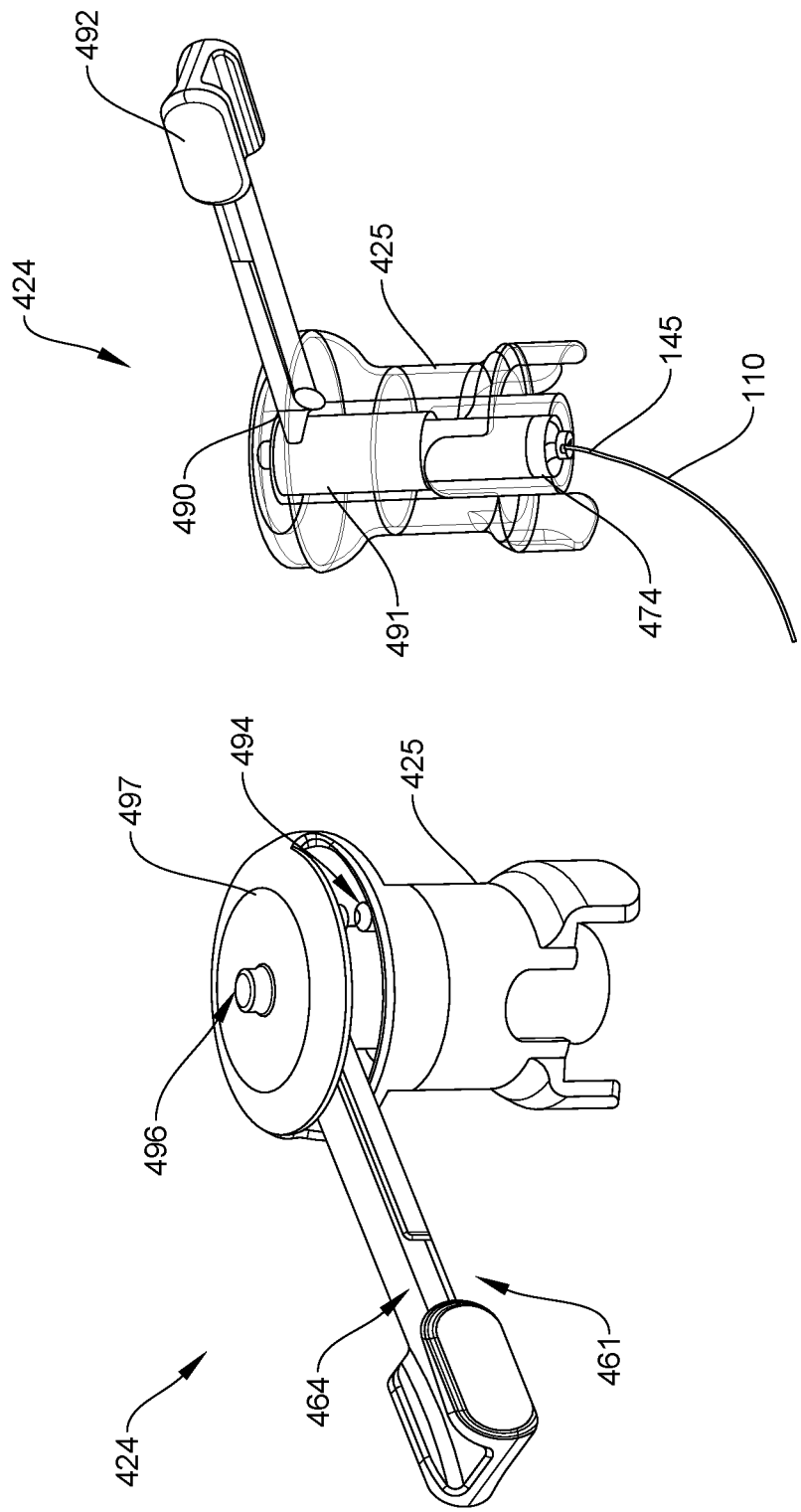

INTERFACE MECHANISM FOR REPOSITIONING AND DEPLOYMENT OF OVER THE SCOPE CLIP

PRIORITY CLAIM

The present disclosure claims priority to U.S. Provisional Patent Application Ser. No. 63/260,412 filed Aug. 19, 2021; the disclosure of which is incorporated herewith by reference

FIELD

The present disclosure relates to endoscopic devices and, in particular, relates to endoscopic clipping devices for treating tissue along the gastrointestinal tract.

BACKGROUND

Physicians have become more willing to perform aggressive interventional and therapeutic endoscopic gastrointestinal (GI) procedures, which may increase the risk of perforating the wall of the GI tract or may require closure of the GI tract wall as part of the procedure. Such procedures may include, for example, the removal of large lesions, tunneling under the mucosal layer of the GI tract to treat issues below the mucosa, full thickness removal of tissue, entering the body via the GI tract and penetrating tissue to exit the GI tract to operate on tissue outside the GI tract, and endoscopic treatment/repair of post-surgical issues (e.g., post-surgical leaks, breakdown of surgical staple lines, and anastomotic leaks).

Currently, tissue may be treated via endoscopic closure devices including through-the scope clips or over-the-scope clips. Over-the-scope clips may be particularly useful for achieving closure of larger tissue defects. These endoscopic closure devices can save costs for the hospital and may provide benefits for the patient. In some cases, however, current endoscopic closure devices may be difficult to use, time consuming to position, or insufficient for certain perforations, conditions and anatomies. For example, current over-the-scope clips generally require launching of the clip from a position in which the clip itself is not visible to the operator. That is, prior to clipping the operator may view the target tissue to be clipped and, based on this visualization of the target tissue may determine that the distal end of the device and the clip are in a desired position relative to the target tissue. Based on the observation of the target tissue, the operator then deploys the clip without being able to see the clip itself until it is deployed.

SUMMARY

The present embodiments are directed to a clipping system for treating tissue comprising a cap configured to be mounted over a distal end of an endoscope, the cap extending longitudinally from a proximal end to a distal end and including a channel extending therethrough so that the cap may be located adjacent to target tissue within a living body. A clip is configured to be mounted over the cap, the clip including first and second jaws movably connected to one via a hinge biased to draw the first and second jaws toward one another, the clip movable relative to the cap between: (a) an insertion configuration, in which the first and second jaws extend over the cap so that the first and second jaws are separated from one another to receive a target tissue therebetween and so that obstruction of an optical system of an endoscope on which the cap is mounted is minimized; (b) a review configuration, in which the clip is moved distally relative to the cap so that a portion of the clip extends distally until at least a portion of the clip extends into a field of view of the optical system of an endoscope on which the cap is mounted; and (c) a deployed configuration in which the clip is moved distally off of the cap so that the first and second jaws are drawn toward one another under the bias of the hinge to close and clip tissue received between the first and second jaws. A control element extends from a distal end releasably coupled to the clip, through the channel of the cap and the endoscope to which it is connected, to a proximal end which, in use, remains outside the living body while the cap is adjacent to the target tissue. The control element is configured so that movement of the control element proximally through the cap moves the clip distally relative to the cap, the control element being configured so that movement of the control element proximally through the cap via a first distance moves the clip from the insertion configuration to the review configuration and movement of the control element proximally through the cap via a second distance moves the clip from the review configuration to the deployed configuration.

In an embodiment, the system may further comprise an actuator assembly connected to a proximal end of the control element, the actuator assembly including a first actuator configured so that, when actuated, the control element is moved proximally through the endoscope via the first distance to move the clip from the insertion configuration to review configuration.

In an embodiment, the first actuator may include first and second longitudinal members pivotally coupled to one another so that when proximal portions of the first and second longitudinal members are drawn toward one another, distal portions of the first and second longitudinal members are correspondingly drawn toward one another.

In an embodiment, the actuator assembly may further include a second actuator configured so that, when actuated, the control element is moved proximally through the endoscope via the second distance to move the clip from the review configuration to the deployed configuration.

In an embodiment, the actuator assembly may further comprise a moving element and a pulley mechanism, the control element being routed through the pulley mechanism to be connected to the moving element so that, when the first and second longitudinal members are drawn toward one another, the moving element is moved from a proximal position relative to a housing of the actuator assembly toward a distal position to pull the control element proximally through the endoscope such that the clip is moved from the insertion configuration toward the review configuration.

In an embodiment, the second actuator may include a push button including a tab extending into a housing of the actuator assembly such that when the clip is in the review configuration, the tab engages a portion of the control element so that pushing the push button exerts an additional tension along the control element which moves the clip from the review configuration toward the deployed configuration.

In an embodiment, the actuator assembly may further comprise a biasing element biasing the first actuator toward the insertion configuration.

In an embodiment, the actuator assembly may include a locking mechanism for locking the clip toward the review configuration.

In an embodiment, the first actuator may include a handle portion configured to be gripped via an operator of the system and a lever movably coupled thereto, the proximal end of the control element connected to the lever so that, when the lever is pressed against the handle portion, the control element is moved proximally through the endoscope via the first distance to move the clip from the insertion configuration toward the review configuration.

In an embodiment, the first actuator may include a housing and a rotary handle rotatably couple thereto, the proximal end of the control element connected to a moving element threadedly coupled to a portion of the rotary handle so that a rotation of the rotary handle relative to the housing moves the control element proximally through the endoscope.

The present embodiments are also directed to a clipping system for treating tissue, comprising an endoscope including a shaft extending longitudinally from a proximal end to a distal end. A cap extending longitudinally from a proximal end to a distal end includes a channel extending therethrough so that the cap is slidably mounted over a distal portion of the shaft of the endoscope. A clip includes first and second jaws movably connected to one another via hinges, at least one of the hinges being biased to draw the first and second jaws toward one another, the clip mountable over the cap such that the first and second jaws extend over opposing portions of the cap so that the first and second jaws are separated from one another to receive a target tissue therebetween. A distal movement of the cap relative to the endoscope from a proximal position along the endoscope to a distal position along the endoscope moves the clip from an insertion configuration toward a review configuration, in which the clip extends distally until at least a portion of the clip extends into a field of view of an optical system of the endoscope. A distal movement of the clip relative to the cap moves the clip from the review configuration toward a deployed configuration, in which the clip is moved distally off of the clip so that the first and second jaws are drawn toward one another under the bias of the at least one hinge to close over tissue received therebetween. A repositioning element extends from a distal end coupled to the cap, through the channel of the cap and the endoscope, to a proximal end that, in use, remains outside the living body. The repositioning element is configured so that moving the repositioning element proximally through the endoscope moves cap distally along the endoscope from the insertion configuration toward the review configuration. A deployment element extends from a distal end releasably coupled to the clip, through the channel of the cap and the endoscope, to a proximal end which, in use, remains outside the living body. The deployment element is configured so that a proximal movement of the deployment element through the endoscope moves the clip distally relative to the cap toward the deployed configuration. An actuator assembly includes a first actuator configured to control a movement of the repositioning element and a second actuator configured to control a movement of the deployment element.

In an embodiment, the actuator assembly may further comprise a housing through which the proximal ends of the repositioning element and the deployment element extend to be connected to the first and second actuators.

In an embodiment, the first actuator may include a lever pivotally coupled to a handle, the proximal end of the repositioning element connected to a portion of the handle so that, when the lever is moved toward the housing, the repositioning element is moved proximally through the endoscope to move the cap and the clip from the insertion configuration toward the review configuration.

In an embodiment, the second actuator may include a push button extending into the housing and connected to the proximal end of the deployment element so that, when the push button is pressed further into the housing, the deployment element is moved proximally through the endoscope to move the clip distally relative to the cap from the review configuration toward the deployed configuration.

In an embodiment, the system may further comprise a biasing element extending between a distal end of the cap and a stop at a distal-most end of an endoscope on which the cap is mounted, the biasing element biasing the cap toward the insertion configuration, in which an entirety of the clip mounted over the cap is proximal of the distal-most end of the endoscope so that when the lever is released, the cap and the clip revert toward the insertion configuration.

The present embodiments are also directed to a method for treating tissue. A clip is inserted to a target area in a body lumen via an endoscope in an insertion configuration in which the clip is mounted over a distal end of an endoscope via a transparent cap, a proximal end of the cap extending over the distal end of the endoscope and a distal portion of the cap extending distally of the distal end of the endoscope, the clip mounted over a proximal portion of the cap so that jaws of the clip are separated from one another, in the insertion configuration. A suction force is applied through a working channel of the endoscope so that tissue is drawn into a channel of the cap and between the jaws of the clip. A first actuator is actuated to move a control element releasably coupled to the clip proximally through the endoscope via a first distance so that the clip is moved toward a review configuration, in which the clip is moved distally along the cap to extend over the distal portion of the cap such that clip is in a field of view of the endoscope in the review configuration. It is determined, when the clip is in the review configuration, whether the clip is in a desired position relative to a target tissue. A second actuator is actuated to apply additional tension to the control element while the clip is in the review configuration so that the control element moves further proximally relative to the endoscope via a second distance to move the clip distally off of the cap toward a deployed configuration, in which the clip reverts toward a biased closed configuration in which the jaws are drawn toward one another to grip the tissue therebetween.

BRIEF DESCRIPTION

FIG. 1 shows a longitudinal side view of a distal portion of a tissue clipping system according to an exemplary embodiment of the present disclosure, in an insertion configuration;

FIG. 2 shows a longitudinal side view of the distal portion of the system of FIG. 1, in a review configuration;

FIG. 3 shows a longitudinal side view of the distal portion of the system of FIG. 1, in a deployed configuration;

FIG. 9 shows a cross-sectional side view of the actuator assembly of FIG. 7, in a first configuration;

FIG. 10 shows a cross-sectional side view of the actuator assembly of FIG. 7, in a second configuration;

FIG. 17 shows a perspective view of an actuator assembly according to yet another exemplary embodiment of the present disclosure;

FIG. 18 shows a transparent perspective view of the actuator assembly of FIG. 17;

DETAILED DESCRIPTION

Figure 6:
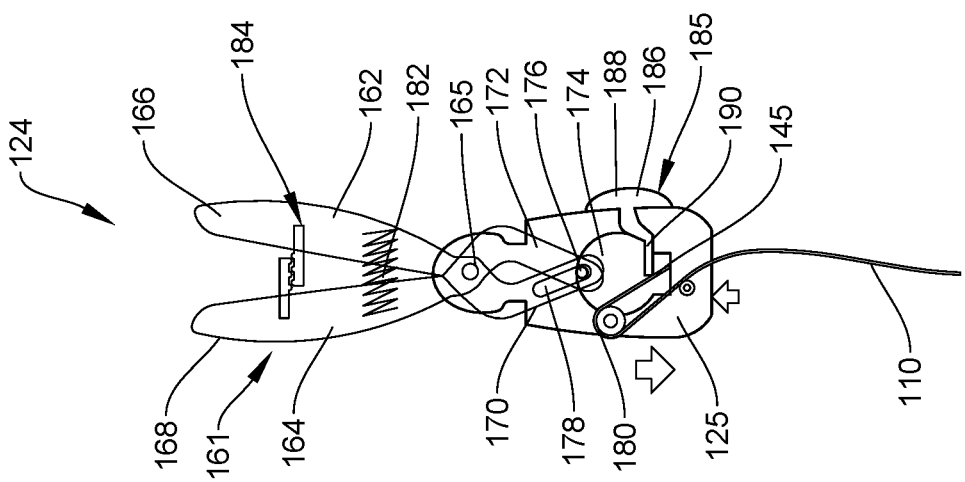
FIG. 6 shows a cross-sectional longitudinal side view of the actuator assembly of FIG. 4, in a second configuration.

The present disclosure may be further understood with reference to the following description and the appended drawings, wherein like elements are referred to with the same reference numerals. The present disclosure relates to a clipping system and, in particular, relates to an over-the-scope endoscopic clipping system, in which an initial placement of a clip may be viewed and adjusted prior to a deployment thereof via an actuator assembly. Exemplary embodiments of the present disclosure comprise a clip mountable over a distal end of an endoscope via cap and an actuator assembly controlling movement of the clip relative to the endoscope between an insertion configuration, a review configuration and a deployed configuration. In the insertion configuration, the clip is mounted over the distal end of the endoscope so that the jaws of the clip are separated from one another toward an open configuration in which tissue may be received therebetween.

In the review configuration, the clip is moved distally relative to the endoscope so that at least a portion of the clip extends within a field of view of the endoscope. In this review configuration, the clip remains mounted over the cap toward the open configuration, with the jaws separated from one another to receive target tissue therebetween, while also being visible via the endoscope so that an operator of the system may determine whether the clip is in a desired position relative to the target tissue. If the clip is determined to be in the desired position relative to the target tissue, the clip may be moved toward the deployed configuration.

In the deployed configuration, the clip is moved distally off of the cap so that the clip reverts toward a biased closed configuration to grip the target tissue between the jaws thereof. The actuator assembly is releasably coupled to the clip via a control element to facilitate movement of the clip relative to the endoscope between the insertion, review and deployed configurations. It will be understood by those of skill in the art, that upon movement of the clip toward the deployed configuration, the clip is entirely separated from the endoscope and is permanently released within the body. It will be understood by those of skill in the art that terms proximal and distal, as used herein, are intended to refer to a direction toward and away from, respectively, a user of the device.

As shown in FIGS. 1-6, a tissue clipping system 100 for treating tissue defects and/or perforations according to an exemplary embodiment of the present disclosure comprises a clip 102 configured to be mounted over a distal end 106 of an endoscope 104 via a transparent cap 108. The clip 102 is releasably coupled to a control element 110 such that tensioning of the control element 110 moves the clip 102 distally relative to the endoscope 104 (and the cap 108 mounted thereon) from an insertion configuration, as shown in FIG. 1, towards a review configuration, as shown in FIG. 2. Upon determination via an operator of the system 100 (e.g., a surgeon) that the clip 102 is in a desired position relative to a target tissue, further tensioning of the control element 110 moves the clip 102 from the review configuration toward a deployed configuration, as shown in FIG. 3, in which the clip 102 is released from the cap 108 and closed over target tissue. In the insertion configuration, as shown in FIG. 1, the clip 102 is mounted over the cap 108 so that the cap 108 holds the clip 102 in an open position with jaws 114 of the clip 102 spread apart from one another about the cap 108 so that tissue to be clipped may be drawn through a channel 116 of the cap 108 and between the jaws 114.

In this insertion configuration, an entirety of the clip 102 (including the jaws 114) of this embodiment is mounted over a proximal portion 138 of the cap 108 minimizing obstruction of the visual field of the optical system of the endoscope 104 so that the user may fully observe the tissue adjacent to the cap 108 through the open end of the cap 108 as well as through the wall of the cap 108. To move the clip 102 from the insertion configuration toward the review configuration, as shown in FIG. 2, the control element 110 is tensioned to push the clip 102 distally along the cap 108 until a portion of the clip 102 abuts a protrusion 120 formed on the cap 108. This provides tactile feedback to the operator indicating that the clip 102 is in the review configuration. In the review configuration, the jaws 114 remain spread out over a distal portion 140 of the cap 108, which extends distally past the distal end 106 of the endoscope 104, with the jaws 114 being maintained open and separated from one another by the cap 108. Since the cap 108 is transparent, when the clip 102 is mounted over the distal portion 140 of the cap 108, the clip 102 is within a field of view of the optical system of the endoscope 104.

In the review configuration, the operator may visually determine whether the clip 102 is in the desired position relative to the target tissue (e.g., a portion of tissue drawn into the cap 108). If, the operator determines that the clip 102 is not in the desired position relative to the target tissue, the tissue may be released from the cap 108 and the distal end 106 of the endoscope 104 is then repositioned until the target tissue is drawn into the cap 108 between the jaws 114 of the clip 102, as desired. When it is determined that the clip 102 is in the desired positioned and the target tissue is drawn into the cap 108 (e.g., by applying suction or a grasper through a working channel of the endoscope 104).

The clip 102 is then deployed by tensioning the control element 110 until a force exerted thereon exceeds a predetermined force which pushes the clip 102 over the protrusion 120, off of the cap 108, as shown in FIG. 3. When the clip 102 is pushed off the cap 108, the jaws 114 of the clip 102 close under their natural bias gripping the tissue that had been drawn into the cap 108. As will be described in further detail below, an actuator assembly 124 at a proximal end of the endoscope 104 is connected to the control element 110 to control the tensioning thereof and a movement of the clip 102 relative to the endoscope 104 between the insertion, review and deployed configurations.

The clip 102 of this embodiment may be mounted to any standard endoscope 104 via the cap 108 which is sized, shaped and configured to be mounted over the distal end 106 of the endoscope 104 (e.g., slid over the distal end 106 and retained thereon via a friction fit). As will be understood by those of skill in the art, the endoscope 104 is configured to be inserted through a body lumen to a target area within the lumen and thus, must be sufficiently flexible to navigate through even tortuous paths of the body lumen although the devices described herein may be configured to operate with any other type of scope or insertion device as would be understood by those skilled in the art.

According to an exemplary embodiment, a proximal end of the endoscope 104 includes a handle member which remains outside the body accessible to a physician or other user permitting the user to guide the endoscope 104 through the body lumen (e.g., gastrointestinal tract) to a target site. In one embodiment, the actuating assembly 124 is coupled to the handle member of the endoscope 104. In another embodiment, the actuating assembly 124 is usable independently of the handle member of the endoscope 104. Although the exemplary embodiments describe use of the clip 102 with the endoscope 104, it will be understood by those of skill in the art that the cap 108 may be sized and shaped to be mounted over the distal end of any insertion device (flexible or rigid) suitable for accessing a target site within a body at which a tissue to be clipped is located.

The cap 108 extends longitudinally from a proximal end 136 to the distal end 118 and includes the channel 116 extending longitudinally therethrough. The cap 108 is configured to be mounted over the distal end 106 of the endoscope 104 so that the channel 116 of the cap 108 is substantially aligned with a longitudinal axis of the endoscope 104 and in communication with a channel of the endoscope 104. The channel 116 extends away from the distal end 106 of the endoscope 104 so that occlusion of the field of view of the endoscope 104 is minimized. The cap 108 is sized and shaped to correspond to a cross-sectional shape of the endoscope 104 so that the cap 108 fits thereover via a friction fit.

The cap 108 is configured so that, when the cap 108 is mounted over the distal end 106 of the endoscope, the proximal portion 138 of the cap 108 extends over an endoscopic shaft while the distal portion 140 of the cap 108 extends distally past the distal end 106 of the endoscope 104. The cap 108 is formed of a transparent material so that portions of the clip 102 extending over the distal portion 140 of the cap 108, or therebeyond, are within the field of view of the endoscope 104. According to one exemplary embodiment, a length of the distal portion 140 of the cap 108 is selected so portions of the clip 102 remain visible even when tissue is suctioned into the cap 108. In one example the distal portion 140 may have a length of approximately 10 mm.

The cap 108 includes one or more protrusions 120 extending from an exterior surface 142 thereof. The protrusions 120 are configured to engage a portion of the clip 102. In one embodiment, the cap 108 includes a pair of protrusions 120 diametrically opposed from one another and positioned along the cap 108 so that, when the clip 102 engages the protrusion 120, the clip 102 extends over the cap 108 in the review configuration. The protrusion 120 is sized, shaped and configured so that, when a distal force exceeding a predetermined threshold value is applied to the clip 102, the clip 102 is moved distally over the protrusion toward the deployed configuration.

The clip 102 includes a pair of jaws 114 connected to one another via hinges 126, which permit movement of the jaws 114 relative to one another between the open configuration, in which the jaws 114 are separated from one another, and the closed configuration, in which the jaws 114 are moved toward one another to grip tissue. Each of the jaws 114 of this embodiment extends along a curve from a first end 128 to a second end 130 so that a first one of the hinges 126 connects the first ends 128 of the jaws 114 to one another, while a second one of the hinges 126 connects the second ends 130 of the jaws 114 to one another. According to one exemplary embodiment, each of the hinges 126 is a living hinge including a groove 132 sized and shaped to engage the protrusion 120 of the cap 108. The hinges 126 in this embodiment are spring biased, biasing the jaws 114 toward the closed configuration. In one exemplary embodiment, each of the jaws 114 includes gripping features such as, for example, teeth 122, so that when the jaws 114 are moved toward one another to the closed configuration, tissue is gripped between the jaws 114 via the teeth 122.

When the clip 102 is mounted over the cap 108, the jaws 114 are stretched open over opposing portions of the cap 108 so that the exterior surface 142 of the cap 108. The cap 108 holds the clip 102 open with the jaws 114 separated from one another in the open configuration so that tissue drawn into the channel 116 of the cap 108 passes between the jaws 114. As would be understood by those skilled in the art, the tissue may be drawn into the channel 116 via, for example, a suction force applied through the endoscope 104 or a grasping device inserted through a working channel of the endoscope 104.

In the insertion configuration, the clip 102 is positioned over the proximal portion 138 of the cap 108. In the review configuration, however, the clip 102 is moved distally relative to the cap 108 until the grooves 132 of the clip 102 engage the protrusions 120 and the clip 102 extends over the distal portion 140 of the cap 108. In one embodiment, the teeth 122 of the clip 102 extend distally past the distal end 118 of the cap 108 in the review configuration. Thus, the clip 102, and the position of the teeth 122 relative to the target tissue, are visible to the operator via the optical system of the endoscope 104.

When the clip 102 is moved distally off the cap 108, the clip 102 reverts to its biased closed configuration to grip between the jaws 114 any tissue that had been drawn into the channel 116. It will be understood by those of skill in the art that the hinges 126 and/or jaws 114 of the clips 102 may be formed of any of a variety of materials so long as the hinges 126 bias the jaws 114 toward the closed configuration, as described above with force sufficient to apply a desired clipping force to the tissue. In one example, portions of the clip 102 (e.g., the hinges 126) may be formed of a shape memory alloy such as, for example, Nitinol.

As described above, the clip 102 may be moved relative to the cap 108 from the insertion configuration toward the review configuration and from the review configuration toward the deployed configuration via the control element 110. The control element 110 may be formed as a thread wire, strand, filament or other similar flexible longitudinal element extending from a distal end 144 releasably coupled to the clip 102 to a proximal end 145 connected to the actuating assembly 124.

According to an exemplary embodiment, the distal end 144 includes an enlarged end which, in one example, is configured as a knot or enlarged end. A distal portion 148 of the control element 110 is looped about a portion of the clip 102 so that a portion of the control element 110 is crimped between the clip 102 and the exterior surface 142 of the cap 108 and the knot engages a portion of the clip 102. A remaining length of the control element 110 extends distally from the clip 102 so that it extends through a distal opening of the channel 116 of the cap 108, proximally through the channel 116 and the working channel of the endoscope 104 to the actuating assembly 124.

In one embodiment, the distal portion 148 of the control element 110 is looped about a first one of the jaws 114 with the knot engaging the clip 102 between two adjacent teeth 122. More specifically, the knot at the distal end 144 of the control element 110 is engaged between the adjacent teeth 122, looped about the first one of the jaws 114 so that a portion of the control element 110 immediately proximal of the knot is crimped between the clip 102 and the exterior surface 142 of the cap 108, the distal portion 148 being looped about the first of the jaws 114 so that the remaining length of the control element 110 extends distally from the clip 102, through the distal opening of the channel 116 of the cap 108, and proximally through the channel 116 and the working channel of the endoscope 104. Thus, when the control element 110 is drawn proximally relative to the endoscope 104, applying a tension thereto, the clip 102 is moved distally relative to the cap 108.

When the clip 102 is mounted over the cap 108 in the insertion configuration, the control element 110 may be drawn proximally relative to the endoscope 104 over a first distance selected so that the grooves 132 of the clip 102 abut the protrusions 120 and the clip 102 is drawn to the review configuration. From the review configuration the control element 110 may be drawn further proximally relative to the endoscope 104 over a second distance, applying a force exceeding the predetermined threshold value, so that the clip 102 moves distally over the protrusion 120 toward the deployed configuration. When the clip 102 is moved distally off of the cap 108 toward the deployed configuration, the distal portion 148 of the control element 110 unravels, disengaging the clip 102 and thereby releasing the clip 102 from the rest of the apparatus, leaving the clip 102 clipped over the target tissue while the scope and the cap 108 are withdrawn from the body. Thus, it will be understood by those of skill in the art that the control element 110 must be able to withstand forces exceeding the predetermined threshold value.

Since, in the review configuration, the clip 102 remains mounted over the cap 108 with the jaws 114 of the clip 102 in the open configuration, if it is determined that the clip 102 is not in a desired position relative to the target tissue, the operator may simply release the tissue from the channel 116 and reposition the distal end 106 of the endoscope 104 as desired. In particular, the distal end 106 may be repositioned until the operator visually confirms that the target tissue has been drawn into the channel 116 between the jaws 114 of the clip 102, as desired. As described above, in the review configuration, the clip 102 extends over the distal portion 148 of the cap 108, distally of the distal end 106 of the endoscope 104 so that the clip 102 is within the field of view of the endoscope 104.

Figure 5:
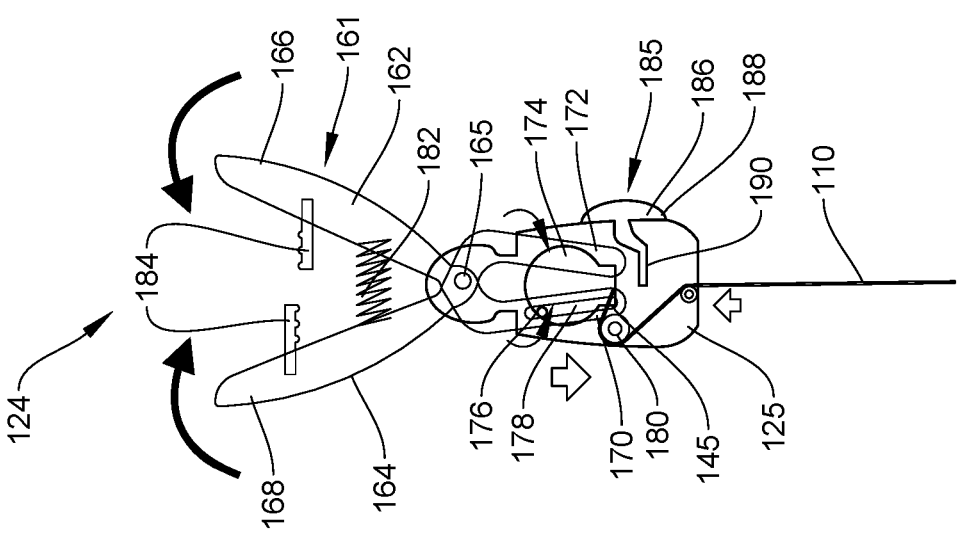
FIG. 5 shows a cross-sectional longitudinal side view of the actuator assembly of FIG. 4, in a first configuration.
Figure 4:
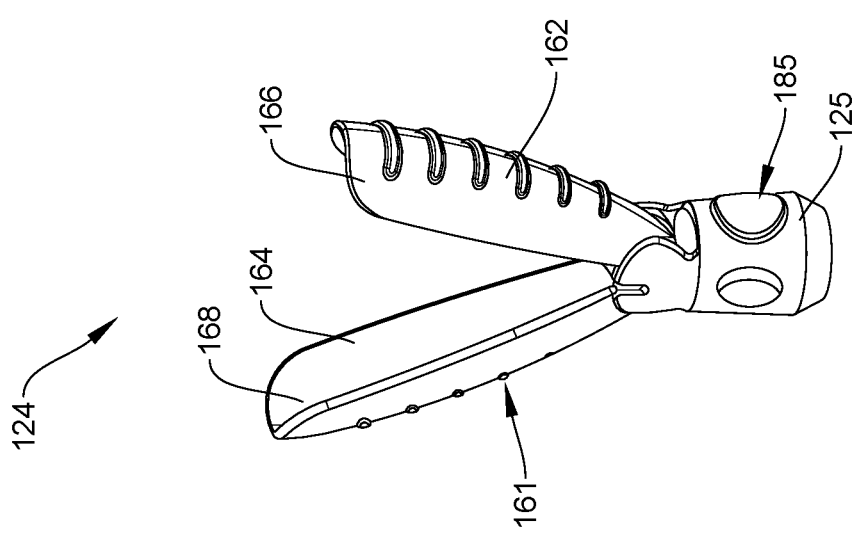
FIG. 4 shows a perspective view of an actuator assembly for controlling movement of a clip according to the system of FIG. 1.
Figure 8:
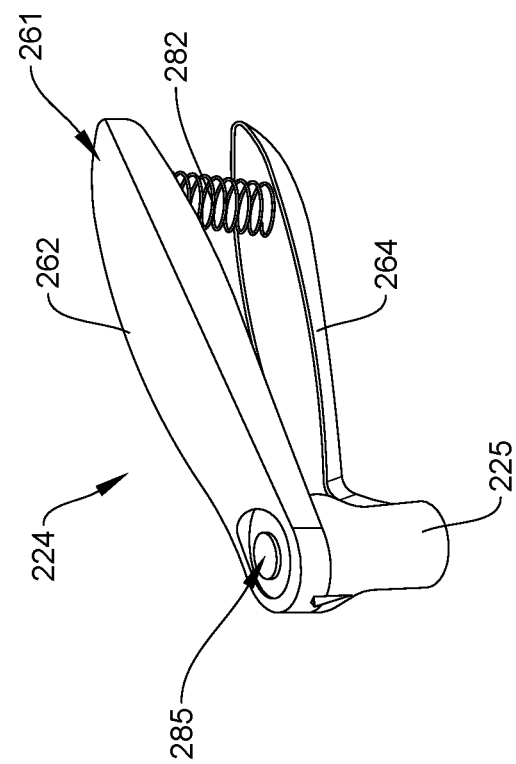
FIG. 8 shows another perspective view of the actuator assembly of FIG. 7.
Figure 7:
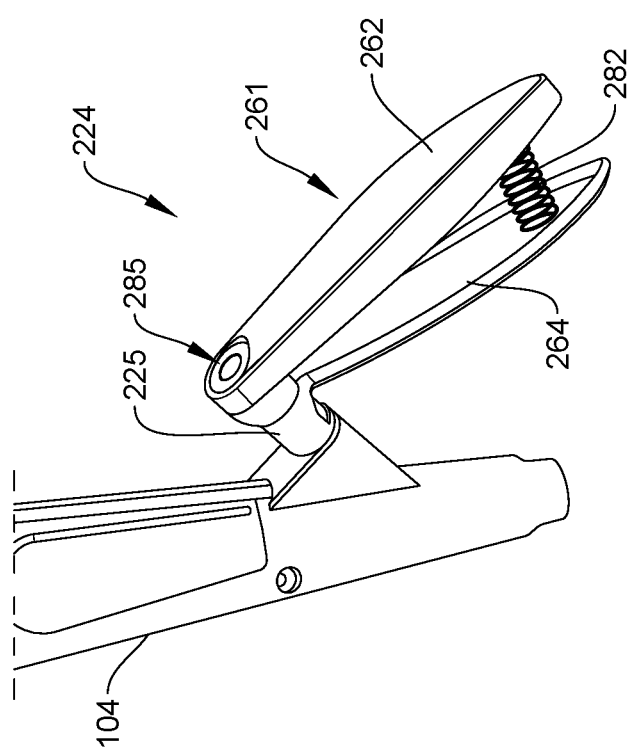
FIG. 7 shows a perspective view of an actuator assembly according to another exemplary embodiment of the present disclosure.

The actuating assembly 124, as shown in FIGS. 4-6, may be used to actuate the control element 110 by applying a tension therealong to move the clip 102 from the insertion configuration to the review configuration and, upon visual confirmation of the desired positioning of the clip 102 relative to the target tissue, from the review configuration toward the deployed configuration. In one embodiment, the actuating assembly 124 may be coupled to the handle member at the proximal end of the endoscope 104 and connected to the proximal end 145 of the control element 110, which extends through the channel of the endoscope 104. In another embodiment, the actuating assembly 124 may be utilized independently of the endoscope 104. In other words, the actuating assembly 124 may be utilized without being directly coupled to any portion of the handle member of the endoscope 104 or any portion of a shaft of the endoscope 104. In particular, the proximal end 145 of the control element 110 may extend out of a proximal end of the endoscope 104 to be connected to the actuating assembly 124.

According to an exemplary embodiment, as shown in FIGS. 4-6, the actuating assembly 124 includes a first actuator 161 for actuating movement of the clip 102 from the insertion configuration toward the review configuration and a second actuator 185 for actuating movement of the clip 102 from the review configuration toward the deployed configuration. In one embodiment, the first actuator 161 includes first and second longitudinal members 162, 164 pivotally coupled to one another and movable relative to one another to move the clip 102 from the insertion configuration toward the review. The first and second longitudinal members 162, 164 are pivotally connected to one another in a substantially scissor-like fashion via, for example, a connecting pin 165 so that when proximal portions 166, 168 of the first and second longitudinal members 162, 164 are drawn toward one another, distal portions 170, 172 are also drawn toward one another. The distal portions 170, 172 are received within a housing 125 and are movably coupled to a moving element 174, which is connected to the proximal end 145 of the control element 110.

In one exemplary embodiment, the distal portions 170, 172 is coupled to the housing 125 via the connecting pin 165 so that the housing 125 is longitudinally fixed with respect to the longitudinal members 162, 164. The distal portions 170, 172, however, may be moved toward and away from one another within the housing 125 and are connected to the moving element 174 so that, when the distal portions 170, 172 are drawn toward each other, the moving element 174 moves from a proximal position relative to the longitudinal members 162, 164 toward a distal position relative to the longitudinal members 162, 164.

In one exemplary embodiment, the moving element 174 is connected to the distal portions 170, 172 via a sliding pin 176 extending from the moving element 174 and received within a longitudinal slot 178 along the distal portion 170 of the first longitudinal member 162. The pin 176 of the moving element 174 is slidably received within the slot 178 so that, when the proximal portions 166, 168 of the first and second longitudinal members 162, 164 are drawn toward one another to correspondingly move the distal portions 170, 172 toward one another, the pin 176 slides distally along the slot 178 to move the moving element 174 from the proximal position to the distal position. It will be understood by those of skill in the art, however, that the moving element 174 may be coupled to the first and second longitudinal members 162, 164 in any of a number of ways so long as the moving element 174 is coupled thereto in a manner that permits a longitudinal sliding of the moving element 174 relative thereto, between the proximal and distal positions, as described above.

In one exemplary embodiment, the proximal portions 166, 168 are biased away from one another via, for example, a compression spring 182. The compression spring 182 prevents the proximal portions 166, 168 from being inadvertently drawn together to move the clip 102 toward the review configuration. In this embodiment, the proximal portions 166, 168 include a ratchet mechanism 184 extending therebetween so that, as the proximal portions 166, 168 are drawn toward one another, the proximal portions 166, 168 are prevented from reverting toward their biased configuration. Thus, once the proximal portions 166, 168 have been drawn toward one another, the moving element 174 is locked in the distal position so that the clip 102 is locked in the review configuration. Upon locking of the proximal portions 166, 168 toward the review configuration, the clip 102 may be visualized and readjusted, as necessary, without having to continually hold the proximal portions 166, 168 toward one another to keep the clip 102 in the review configuration.

As shown in FIG. 5-6, the control element 110 is routed through a pulley mechanism 180 within the housing 125 to be coupled to the moving element 174. In particular, the control element 110 extends from the distal end 144 connected to the clip 102, through the endoscope 104 and through the housing 125 to be routed through the pulley mechanism 180 so that the proximal end 145 is connected to the moving element 174. The pulley mechanism 180 is configured so that when the moving element 174 is moved from the proximal position to the distal position, the proximal end 145 of the control element 110 is moved proximally, moving the control element 110 along the pulley mechanism 180 so that tension is applied to the control element 110. The first and second longitudinal members 162, 164 are configured so that when the proximal portions 166, 168 are drawn toward one another, a tension applied to the control element 110 is sufficient to move the clip 102 from the insertion configuration to the review configuration, a portion of the clip 102 engaging the protrusion 120.

In one embodiment, the pulley mechanism 180 is positioned within a portion of the housing 125 that is substantially longitudinally aligned with the proximal end 145 of the control element 110 when the moving element 174 is in the proximal position (see FIG. 5). When the proximal portions 166, 168 are drawn toward one another and the moving element 174 is moved toward the distal position, however, the proximal end 145 of the control element 110 is also moved distally so that a portion of the control element 110 extends from the pulley mechanism 180 along a portion of the housing 125 that is in communication with second actuator 185 (see FIG. 6).

The second actuator 185 for actuating movement of the clip 102 from the review configuration toward the deployed configuration, in one exemplary embodiment, includes a push button 186. The push button 186 includes a push portion 188 accessible to the user along an exterior of the housing 125 and a tab 190 extending into the housing 125. As shown in FIG. 6, when the moving element 174 is moved from the proximal position toward the distal position, a portion of the control element 110 is moved into engagement with the tab 190 of the push button 186 while the tension is being applied along the control element 110. Thus, when it is desired to move the clip 102 from the review configuration toward the deployed configuration, the operator of the system 100 presses the push portion 188 so that the tab 190 is moved further into the housing 125 and pressed into the portion of the control element 110 with which it is engaged. Thus, when the push portion 188 is pressed, the tab 190 is pressed further into the control element 110, applying additional tension along the control element 110 which causes a length of the control element 110 extending through the endoscope to be moved proximally relative to the endoscope 104 at a force sufficient to move the clip 102 distally over the protrusion 120 along the cap 108, from the review configuration toward the deployed configuration. As the clip 102 is pushed distally off of the cap 108, the clip 102 reverts toward its biased configuration to be clipped over the target tissue.

According to an exemplary method for tissue closure utilizing the system 100, as shown in FIGS. 1-6, the endoscope 104 with the cap 108 and the clip 102 mounted thereon are inserted into a natural body orifice into and through a body lumen such as, for example, the gastrointestinal tract, to a target area within the lumen. As described above, in the insertion configuration, as shown in FIG. 1, the clip 102 is mounted over the proximal portion 138 of the cap 108, which is mounted over the distal end 106 of the endoscope 104, so that the jaws 114 are separated from one another toward the open configuration. The clip 102 is guided to the target area via the endoscope 104, and positioned over target tissue. The target tissue is then drawn into the cap 108 via, for example, a suction force applied through a working channel of the endoscope 104.

The clip 102 is then moved toward the review configuration by moving the clip 102 distally relative to the cap 108 utilizing the first actuator 161. In particular, the proximal portions 166, 168 of the first and second longitudinal members 162, 164 are moved toward one another so that the moving element 174, to which the proximal end 145 of the control element 110 is attached, is moved from the proximal position toward the distal position, as described above. The first and second longitudinal members 162, 164 may then be locked relative to one another via the ratchet mechanism 184 so that the clip 102 is locked toward the review configuration. In the review configuration, the clip 102 extends over the distal portion 140 of the cap 108 so that a position of the clip 102 relative to the target tissue is within the field of view of the endoscope 104. Thus, in the review configuration, the user determines whether the clip 102 is in the desired gripping position relative to the target tissue.

As discussed above, the actuating assembly 124 may be locked toward the review configuration. Thus, if it is determined during the review configuration that the clip 102 is not in the desired position relative to the target tissue, the tissue drawn into the cap 108 is released therefrom and the distal end 106 of the endoscope 104, and thereby the clip 102, are repositioned over the target tissue. The clip 102 may be repeatedly repositioned relative to the target tissue, as necessary during the review configuration, until the user is able to visually confirm that the clip 102 is positioned over the target tissue, as desired.

Once the user confirms that the target tissue has been drawn into the channel 116 between the jaws 114, as desired, the clip 102 may be moved from the review configuration to the deployed configuration via the second actuator 185 to move the clip 102. In particular, the operator presses the push button 186 so that the tab 190 extends further into the portion of control element 110 in engagement therewith. A force exerted on the control element 110 via the tab 190 exceeds a predetermined threshold level, which allows the clip 102 to be moved distally over the protrusion 120 of the cap 108 toward the deployed configuration. The clip 102 is moved distally relative to the cap 108 until the clip 102 is moved distally off the cap 108 and the clip 102 reverts to its biased closed configuration gripping the target tissue. As described above, when the clip 102 is moved toward the deployed configuration, the control element 110 disengages the clip 102 releasing the clip 102 in the body, clipped over the target tissue as the endoscope 104 and the cap 108 are withdrawn from the body.

As shown in FIGS. 7-10, an actuator assembly 224 according to another exemplary embodiment is substantially similar to the actuator assembly 124 and is similarly utilized with the clip 102 and the endoscope 104, as described above with respect to the system 100. Similarly to the actuator assembly 124, the actuator assembly 224 comprises a first actuator 261 for moving the clip 102 from the insertion configuration toward the review configuration and a second actuator 285 for moving the clip 102 from the review configuration toward the deployed configuration. Similarly to the actuator assembly 124, the actuator assembly 224 may, in one embodiment, be coupled to a handle of the endoscope 104 to be utilized therewith. In another embodiment, the actuator assembly 224 may utilized independently (i.e., without direct coupling to the handle of the endoscope 104) to control movement of the control element 110 and thereby the clip 102.

Rather than having pivotally engaged components, however, the first actuator 261 may include a lever 264 movable relative to a handle portion 262 to move the control element 110. The proximal end 145 of the control element 110 is connected to an end of the lever 264 so that, when the lever 264, is pressed, the control element 110 is moved proximally relative to the endoscope 104, thereby moving the clip 102 distally along the cap 108 from the insertion configuration toward the review configuration. The lever 264 should remain pressed to maintain the tension along the control element 110 toward the review configuration. In one embodiment, similarly to the first actuator 161, the lever 264 may be biased away from the handle portion 262 via, for example, a compression spring 282 extending therebetween. Thus, the actuator assembly 224 may further include a lock 284 for locking the lever 264 relative to the handle portion 262 toward the review configuration.

Similarly to the actuator assembly 124, the actuator assembly 224 includes a pulley mechanism 280 within a housing 225 thereof through which a proximal portion of the control element 110 is routed to be connected to the lever 264. The pulley mechanism 280 routes the control element 110 through the housing 225 so that the control element 110 interfaces with the second actuator 285. Thus, when it is desired to move the clip 102 from the review configuration toward the deployed configuration, the second actuator 285 is employed to provide a further tension to the clip 102, which is sufficient to move the clip 102 distally over the protrusion 120 of the cap 108. Similarly to the second actuator 185, the second actuator 285 includes a push button 286. The push button 286 includes a push portion 288 accessible to the user along an exterior of the housing 225 and a tab 290 extending into the housing 225.

As shown in FIGS. 9-10, when it is desired to move the clip 102 from the review configuration toward the deployed configuration, the push portion 288 is pressed moving the tab 290 further into the housing 225 and pressing it against the control element 110. Thus, when the push portion 288 is pressed, the tab 290 is pressed further into the control element 210, applying additional tension along the control element 110 moving causes a length of the control element 110 extending through the endoscope proximally relative to the endoscope 104 at a force sufficient to move the clip 102 distally over the cap 108 past the protrusion 120 from the review configuration toward the deployed configuration. As the clip 102 is pushed distally off of the cap 108, the clip 102 is reverts to its biased configuration clipping the tissue drawn into the cap 108.

Figures 11, 12:
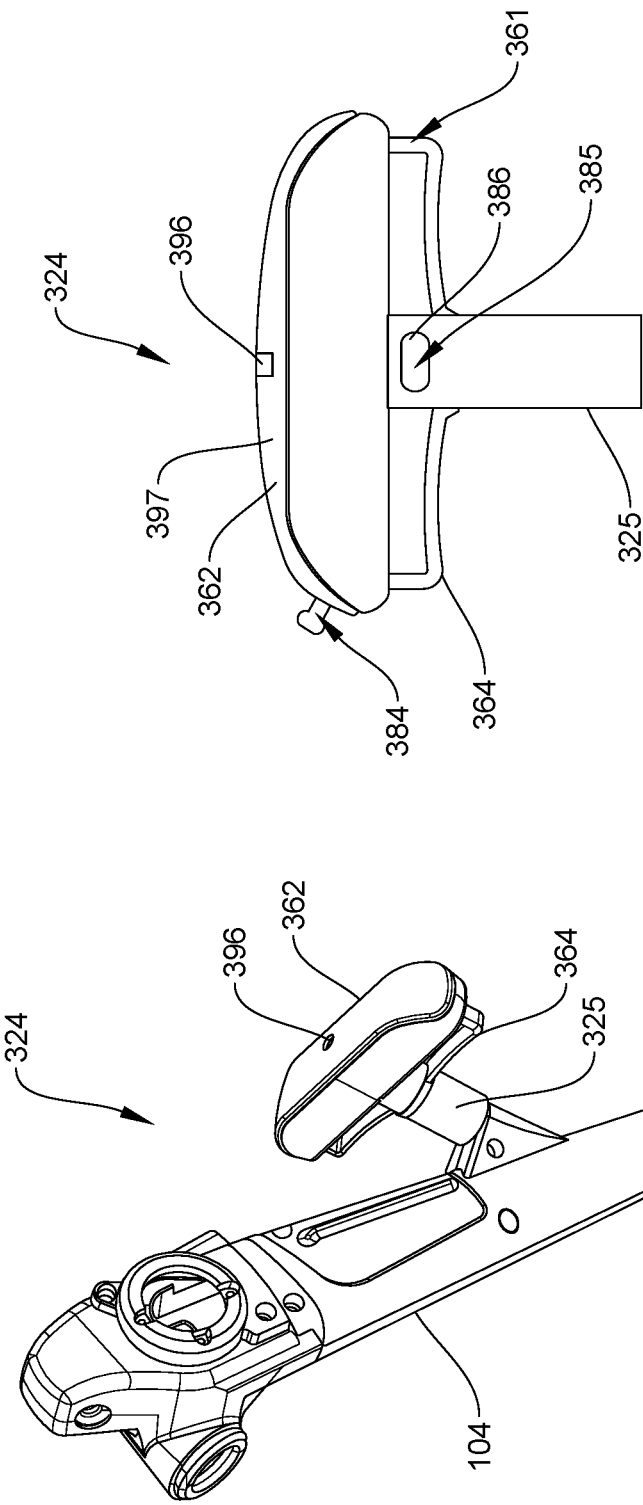
FIG. 11 shows perspective view of an actuator assembly according to another exemplary embodiment of the present disclosure.
FIG. 12 shows a side view of the actuator assembly of FIG. 11.
Figure 14:
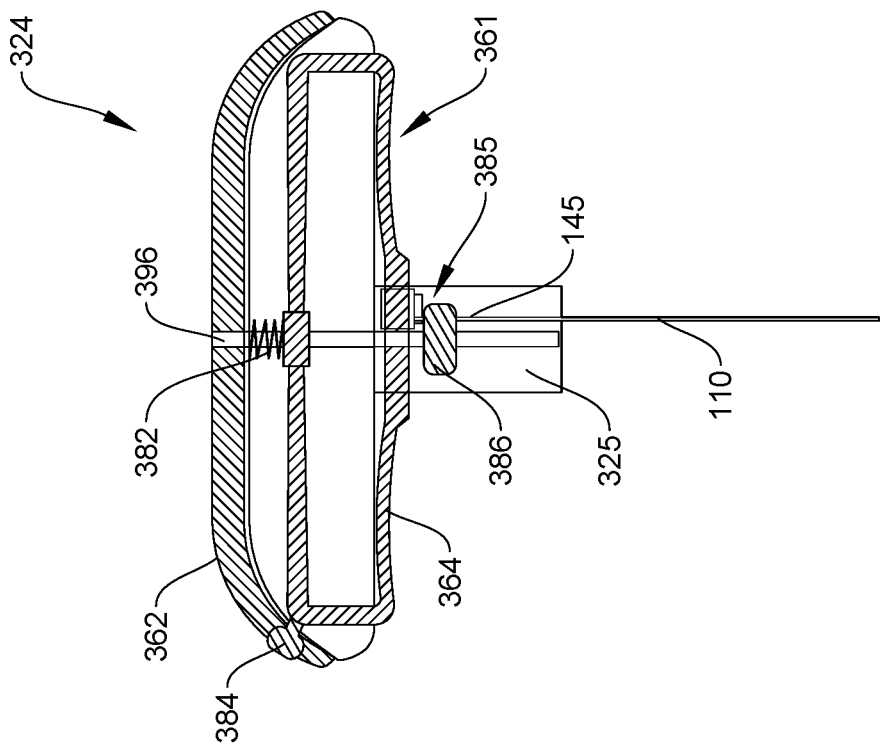
FIG. 14 shows a cross-sectional side view of the actuator assembly of FIG. 11, in a second configuration.
Figure 13:
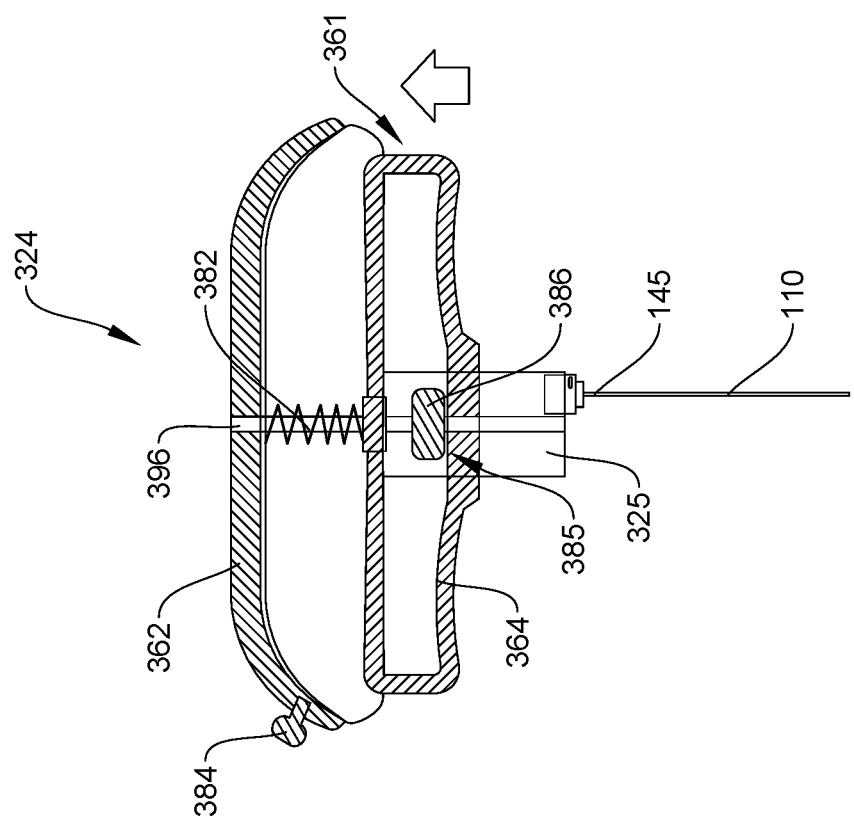
FIG. 13 shows a cross-sectional side view of the actuator assembly of FIG. 11, in a first configuration.

As shown in FIGS. 11-16, an actuator assembly 324 according to another exemplary embodiment is substantially similar to the actuator assemblies 124, 224, and may be utilized with the clip 102 and the endoscope 104, as described above with respect to the system 100 for actuating movement of the clip 102 between the insertion configuration, review configuration and deployed configuration. Similarly to the actuator assemblies 124, 224, the actuator assembly 334 comprises a first actuator 361 configured to move the clip 102 from the insertion configuration to the review configuration and a second actuator 385 configured to move the clip 102 from the review configuration toward the deployed configuration. The actuator assembly 324 may be coupled to the endoscope 104, as shown in FIG. 11, or may be utilized independently of the endoscope, as shown in FIG. 12.

A handle portion 362 in this embodiment is, for example, an ergonomic, substantially T-shaped handle configured to be gripped by the operator of the system 100. In particular, in one embodiment, a handle portion 362 extends substantially perpendicularly to a housing portion 325 through which the control element 110 extends from the endoscope 104. Further, rather than a long lever or handle as described above with respect to the actuator assemblies 124, 224, the first actuator 361 in this embodiment includes a lever 364 extending along the handle portion 362 so that the lever 364 may be gripped there against via a power grip. The proximal end 145 of the control element 110 is connected to the lever 364 so that, when it is pressed against the handle portion 362, a length of the control element 110 passing through the endoscope 104 is moved proximally relative to the endoscope 104, moving the clip 102 distally along the cap 108 from the insertion configuration toward the review configuration.

Figure 16:
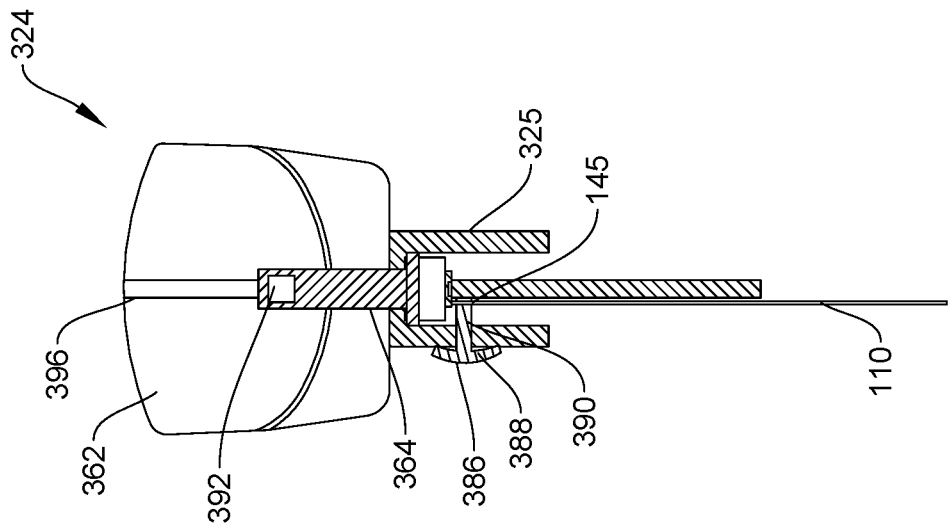
FIG. 16 shows another cross-sectional side view of the actuator assembly of FIG. 11, in the second configuration.
Figure 15:
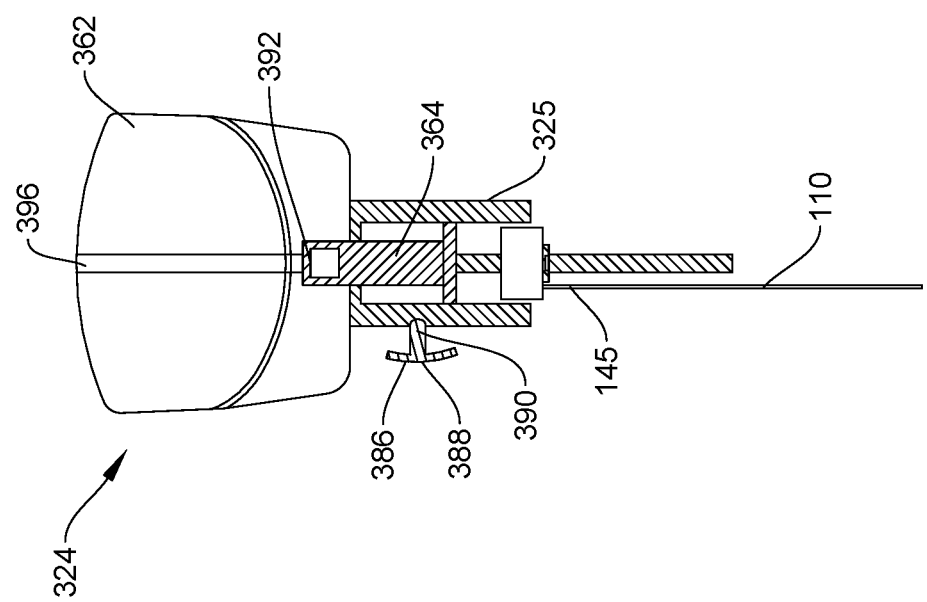
FIG. 15 shows another cross-sectional side view of the actuator assembly of FIG. 11, in the first configuration.
Figure 20:
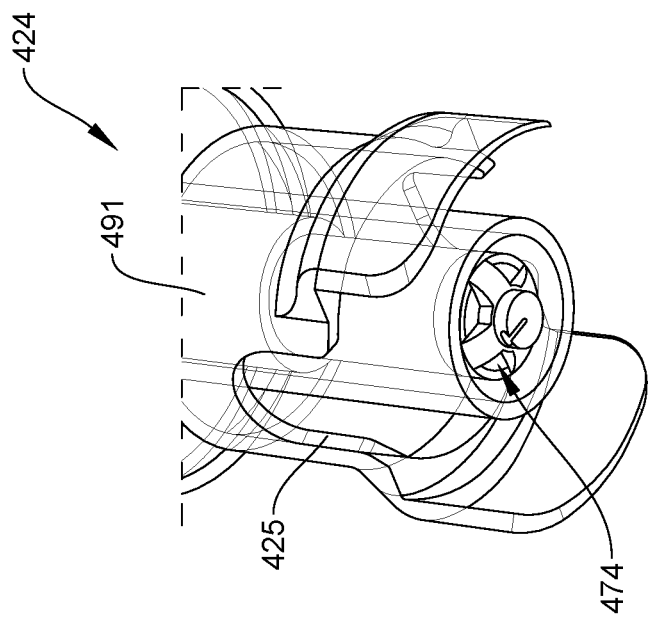
FIG. 20 shows a transparent perspective view of a distal portion of the actuator assembly of FIG. 17.
Figure 19:
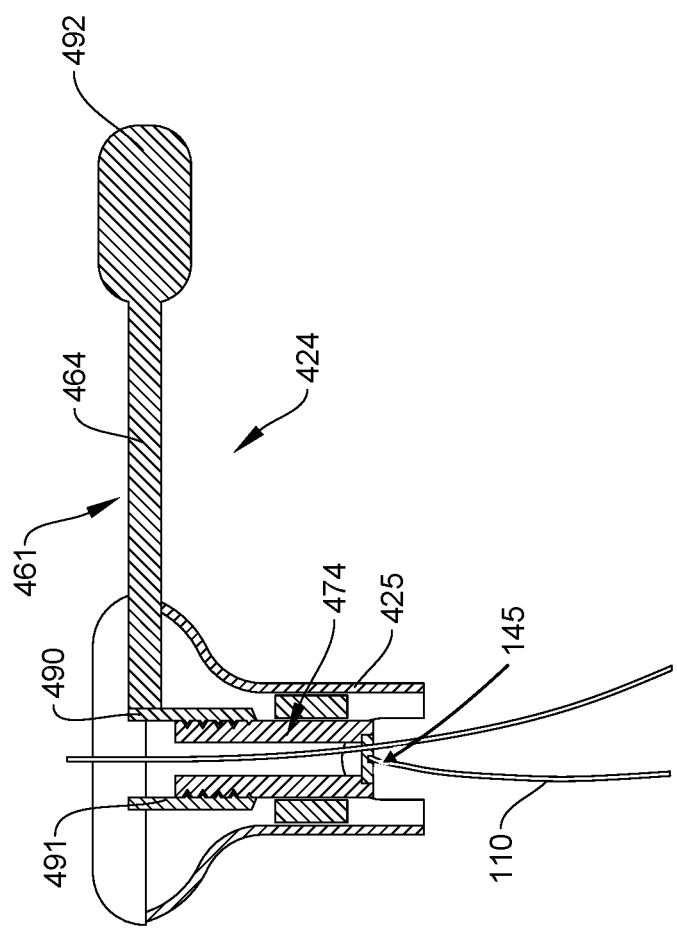
FIG. 19 shows cross-sectional side view of the actuator assembly of FIG. 17.

Similarly to the previously described actuator assemblies, the lever 364 is biased away from the handle portion 362 via, for example, a compression spring 382 extending between the handle portion 362 and the lever 364. To maintain a tension along the control element 110 and to lock the clip 102 toward the review configuration, the actuator assembly 324 further includes a lock 384. The lock 384, in this embodiment, includes a button located on the handle portion 362 so that, when pressed thereinto, a portion of the button engages a portion of the lever 364 received within the handle portion 362 to engage the lever 364 and hold the lever 364 relative to the handle portion 362 in a position corresponding to the review configuration. (see FIG. 14). In particular, as shown in FIG. 16, a portion of the button of the lock 384 extends into and engages a slot 392 within the lever 364 to lock the lever 364 relative to the handle portion 362.

As the control element 110 is drawn proximally relative to the endoscope 104 from the insertion configuration toward the review configuration, a proximal portion of the control element is drawn proximally past a portion of the housing 325 which interfaces with the second actuator 385. Similarly to the previously described actuator assemblies, the second actuator 385 in this embodiment includes a push button 386 including a push portion 388 and a tab 390 extending into the housing 325. When it is desired to move the clip 102 from the review configuration toward the deployed configuration, the operator pushes the push portion 388 moving the tab 390 further into the housing 325 so that the tab 390 is pressed against the control element 110 imparting additional tension to the control element 110. This tension moves a length of the control element 110 extending through the endoscope 104 proximally relative to the endoscope 104 at a force sufficient to move the clip 102 distally over the protrusion 120, from the review configuration toward the deployed configuration. As the clip 102 is pushed distally off of the cap 108, the clip 102 reverts toward its biased configuration to be clipped over the target tissue.

While the exemplary embodiments show and describe target tissue being drawn into the channel 116 of the cap 108 via suction applied through, for example, the working channel of the endoscope 104, it will be understood by those of skill in the art that tissue may also be drawn into the channel 116 using other methods. For example, in other embodiments, tissue may be drawn into the channel and between the separated jaws 114 of the clip 102, when the clip 102 is in, for example, the review configuration, by using devices such as tissue graspers passed through the endoscope 104 to the distal end 106 thereof. The actuator assembly 324 further includes a port 396 extending through a proximal end 397 of the housing 325 configured to receive devices such as tissue graspers therein. Tissue graspers may be inserted through the port 396 and through the working channel of the endoscope 104 so that tissue adjacent the distal end 106 may be drawn into the channel 116 of the cap 108, substantially as described above with respect to the system 100. In one embodiment, tissue graspers (or other similar devices) are inserted into the port 396 and through a corresponding channel extending through the housing 325 and lever 364.

As shown in FIGS. 17-20, an actuator assembly 424 according to another exemplary embodiment is substantially similar to the actuator assemblies described above. The actuator assembly 424 may be utilized to control movement of the clip 102 relative to the endoscope 104, as described above with respect to the system 100. The actuator assembly 424, however, comprises a single actuator 461 capable of controlling both the movement of the clip 102 from the insertion configuration to the review configuration and the movement of the clip 102 from the review configuration toward the deployed configuration.

According to an exemplary embodiment, the actuator assembly 424 includes a rotary handle 464 rotatable about a housing 425 through which the control element 110 is received from the endoscope 104. The rotary handle 464 extends from a first end 490 coupled to the housing 425 to a second end 492 that remains accessible to the operator of the system so that the rotary handle 464 may be rotated about the housing 425. In one embodiment, the first end 490 includes a coupling member 491 rotatably received within the housing 425 and configured to receive therein a moving element 474. The moving element 474 in this embodiment is threadedly received within the coupling member 491 of the rotary handle 464 so that, when the rotary handle 464 is rotated about the housing 425, the moving element 474 is moved longitudinally relative to the housing 425 as it rotates.

In one embodiment, when the rotary handle 464 is rotated in a first direction relative to the housing 425, the moving element 474 moves proximally relative to the housing. The proximal end 145 of the control element 110 is connected to the moving element 474. Thus, when the rotary handle 464 is rotated in the first direction, the control element 110 moves proximally relative to the housing 425, and thereby the endoscope 104, to move the clip 102 distally along the cap 108.

Similarly to the actuator assemblies described above, the actuator assembly 424 includes, for example, a compression spring or other biasing element biasing the rotary handle toward the insertion configuration. To move the clip 102 toward the review configuration, the operator actively rotates the rotary handle. In one exemplary embodiment, the housing 425 includes a pin 494 or other protrusion along a portion of the housing 425. The pin 494 interfaces with the rotary handle 464 as the rotary handle 464 is rotated about the housing 425. The pin 494 is positioned along the housing 425 so that, as the rotary handle 464 is rotated about the housing 425, the rotary handle 464 engages the pin 494 until the control element 110 has been moved by a proximal distance sufficient to move the clip 102 from the insertion configuration toward the review configuration.

Engagement between the pin 494 and the rotary handle 464 provides tactile feedback to the operator indicating the clip 102 is engaged with the protrusion 120 along the cap 108 and is in the review configuration. When it is desired to move the clip 102 from the review configuration toward the deployed configuration, the operator further rotates the rotary handle 464 about the housing 425 in the first direction, pushing the rotary handle 464 past the pin 494. As the rotary handle 464 is rotated past the pin 494, the clip 102 is correspondingly pushed distally beyond the protrusion 120 until the clip 102 is pushed distally off of the cap 108 and permitted to revert to its biased closed configuration to grip the target tissue.

Similarly to the actuator assembly 324, the actuator assembly 424 further includes a port 496 extending through a proximal end 497 of the housing 425 configured to receive devices such as tissue graspers therein. Tissue graspers may be inserted through the port 496 and through the working channel of the endoscope 104 so that tissue adjacent the distal end 106 may be drawn into the channel 116 of the cap 108, substantially as described above with respect to the system 100. In one embodiment, tissue graspers (or other similar devices) may be inserted into the port 496 and through a corresponding channel extending through the moving element 474 to be received within the endoscope 104.

Figure 23:
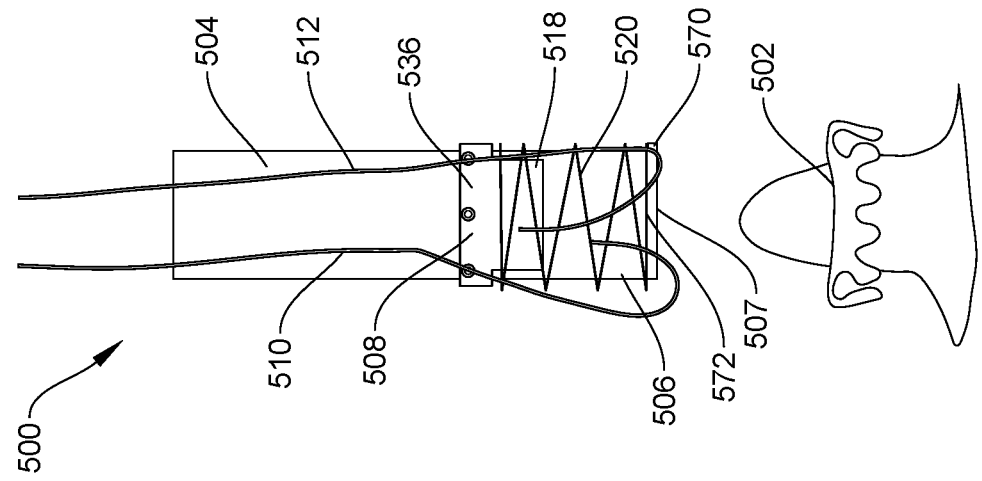
FIG. 23 shows a longitudinal side view of the distal portion of the system of FIG. 21, in a review configuration.
Figure 22:
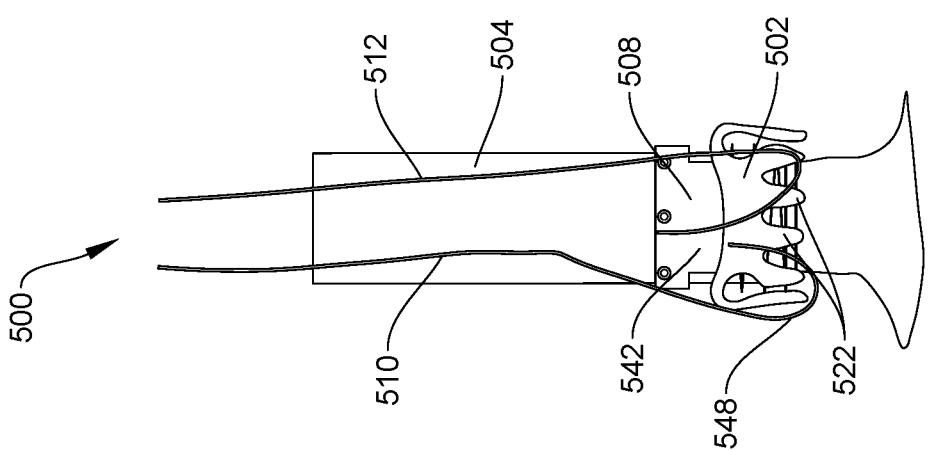
FIG. 22 shows a longitudinal side view of the distal portion of the system of FIG. 21, in a review configuration.
Figure 21:
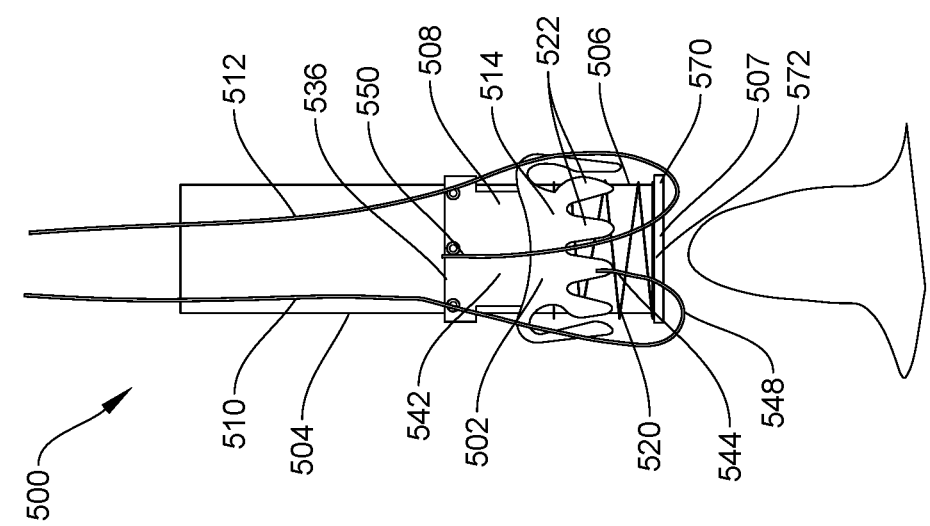
FIG. 21 shows a longitudinal side view of a distal portion of a tissue clipping system according to another exemplary embodiment of the present disclosure, in an insertion configuration.

As shown in FIGS. 21-25, a tissue clipping system 500 according to another exemplary embodiment is substantially similar to the system 100, comprising a clip 502 mountable over a distal end 506 of an endoscope 504 via a cap 508 so that the clip 502 is movable relative to the endoscope 504 between an insertion configuration, a review configuration and a deployed configuration. Similarly to the system 100, the clip 502 may be moved from the insertion configuration, as shown in FIG. 21, to the review configuration, as shown in FIG. 22, and then, upon confirmation that the target tissue is received between jaws 514 of the clip 502 as desired, the clip 502 is moved from the review configuration toward the deployed configuration, as shown in FIG. 23. The system 500, however, is configured such that, if during the review configuration, an operator of the system 500 determines that the clip 502 is not in a desired position relative to the target tissue, the clip 502 may be moved from the review configuration back toward the insertion configuration so that the distal end 506 and the clip 502 may be repositioned relative to the target tissue when the clip 502 is in the insertion configuration.

The system 500 thus further comprises a repositioning element 512 configured to facilitate movement of the clip 502 between the insertion configuration and the review configuration and a deployment element 510 configured to facilitate movement from the review configuration toward the deployed configuration, when it is determined that the clip 502 is in a desired position relative to the target tissue. As described above, the deployment element 510 and the repositioning element 512 are connected to an actuator assembly 524 substantially similar to the actuator assemblies 124-324 described above with respect to the system 100. The actuator assembly includes a first actuator 561 for moving the clip 502 between the insertion configuration and the review configuration, and a second actuator 585 for moving the clip 502 from the review configuration toward the deployed configuration.

Similarly to the system 100, in the insertion configuration the clip 502 is mounted over the cap 508 in the open configuration with the jaws 514 thereof separated from one another to receive tissue therebetween. The clip 502 is preferably inserted to a target site within a body in this insertion configuration. The clip 502 may be moved from the insertion configuration to the review configuration, by moving the clip 502 distally relative to the endoscope 504 to enhance a field of view of the endoscope 504 so that a position of the clip 502 relative to the target tissue is visible to an operator (e.g., surgeon or other user) of the system 500.

Rather than moving the clip 502 relative to the cap 508, however, the cap 508—with the clip 502 mounted thereon—is moved distally relative to the endoscope 504 to move the clip 502 from the insertion configuration toward the review configuration. The clip 502 is mounted over the cap 508 such that a portion of the clip 502 extends distally past a distal end 518 of the cap 508 while maintaining the clip 502 in the open position so that, when the cap 508 is moved distally relative to the endoscope 504 toward the review configuration, a portion of the clip 502 extends distally of the distal end 506 of the endoscope 504 so that the portion of the clip 502 extending distally beyond the distal end 506 is within the field of view of the endoscope 504.

If the operator determines that the clip 502 is in a desired position relative to the target tissue, the clip 502 may be moved from the review configuration toward the deployed configuration. If, however, the operator determines that the clip 502 is not in the desired position relative to the target tissue, the clip 502 may be moved from the review configuration back toward the insertion configuration so that any tissue drawn into the cap 508 may be released and the clip 502 may be repositioned as desired relative to the target tissue.

To facilitate movement of the cap 508 and clip 502 relative to the endoscope 504 between the insertion configuration and the review configuration, the system 500 further comprises a biasing element 520 extending between the cap 508 and a distal-most end 507 of the endoscope 504 to bias the cap 508, and the clip 502 mounted thereover, toward the insertion configuration. The repositioning element 512, a distal end 550 of which is connected to the cap 508, may be used to move the cap 508 and clip 502 between the insertion configuration and the review configuration, as necessary, until the operator determines that the clip 502 is in the desired configuration relative to the target tissue.

Once the operator has determined that the clip 502 is in the desired position relative to the target tissue, the deployment element 510, a distal end 544 of which is releasably coupled to the clip 502, may be used to move the clip 502 distally off of the cap 508 toward the deployed configuration. In the deployed configuration, the clip 502 reverts under its natural bias toward the closed configuration to grip the target tissue received between the jaws 514. Manipulation of the deployment element 510 and/or the repositioning element 512 for moving the clip 502 between the insertion, review and deployed configurations may be controlled via an actuator assembly 524 at a proximal end of the endoscope 504.

Those skilled in the art will understand that the endoscope 504 may be substantially similar to the endoscope 104 and extends longitudinally from a proximal end including a handle member 534 to the distal end 506, over which the cap 508 is mounted. The endoscope 504 includes a channel 505 extending therethrough. In this embodiment, the endoscope 504 further includes a stop 570, shoulder or other protrusion extending from an exterior surface 542 of the cap 508, at the distal-most end 507, for engaging a distal end 572 of the biasing element 520 and stopping the distal end 572 of the biasing element 520 from extending distally beyond the stop 570.

The cap 508 may also be substantially similar to the cap 108, extending longitudinally from a proximal end 536 to a distal end 518 and defining a channel 516 therein. The channel 516 corresponds to a size of the endoscope 504 so that the cap 508 may be movably mounted thereover. In one embodiment, the cap 508 also includes an opening extending through a wall thereof, the opening configured to receive the repositioning element 512 therein, as will be described in further detail below.

The biasing element 520 of this embodiment extends between the distal end 518 of the cap 508 and the stop 570 of the endoscope 504 to bias the cap 508 toward the insertion configuration. According to one exemplary embodiment, the biasing element 520 may be configured as a spring extending about the distal end 506 of the endoscope 504, between the distal end 518 of the cap 508 and the stop 570 at the distal-most end 507 of the endoscope 504. In the insertion configuration, the clip 502, which is substantially similar to the clip 102, is mounted over the cap 508 so that jaws 514 of the clip 502 are stretched open over the cap 508.

The exterior surface 542 of the cap 508 holds the jaws 514 open so that the jaws 514 are separated from one another and tissue may be received therebetween. The clip 502 may be mounted over the cap 508 so that, for example, teeth 522 extend distally past the distal end 518 of the cap 508. In the insertion configuration, however, the distal end 518 of the cap 508 is separated from the distal-most end 507 of the endoscope 504 via a distance selected so that the teeth 522 do not extend distally past the distal-most end 507 of the endoscope 504.

To move the clip 502 toward the review configuration, the cap 508 is moved distally relative to the endoscope 504, compressing the biasing element 520 until the teeth 522 extend distally past the distal-most end 507 of the endoscope 504 so that the teeth 522 is within the field of view of the endoscope 504. Thus, in the review configuration, the operator or user may determine whether the clip 502 is in the desired position relative to the target tissue. If the clip 502 is in the desired position, the clip 502 may be moved toward the deployed configuration by pushing the clip 502 distally off of the cap 508.

If, however, it is determined that the clip 502 is not in the desired position relative to the target tissue, the compression force on the biasing element 520 is released so that the biasing element 520 reverts to its biased configuration, pushing the cap 508 proximally along the endoscope 504 toward the insertion configuration so that any tissue previously drawn into the cap 508 may be released and the clip 502 may be repositioned. As will be described in further detail below, movement of the clip 502 between the insertion configuration and the review configuration is controlled via the repositioning element 512 and movement of the clip 502 from the review configuration toward the deployed configuration is controlled via the deployment element 510.

The deployment element 510 of this embodiment is substantially similar to the control element 110 includes, for example, a thread, wire, strand, filament or other similar flexible longitudinal element extending from the distal end 544 releasably coupled to the clip 502 to a proximal end connected to the actuator assembly 524. The deployment element 510 of this embodiment is releasably coupled to the clip 502 in a manner substantially to the coupling between the clip 102 and the control element 110. In an exemplary embodiment, a distal portion 548 of the deployment element 510 is looped about a portion of a first one of the jaws 514 so that a portion of the deployment element 510 is crimped between the clip 502 and the exterior surface 542 of the cap 508 while, for example, a knot or other enlargement, at the distal end 544 is engaged between adjacent teeth 522 of a first one of the jaws 514.

A remaining length of the deployment element 510 extends distally from the clip 502 to pass through a distal opening of the channel of the endoscope 504 and extend proximally through the endoscope 504. Thus, drawing the deployment element 510 proximally relative to the endoscope 504 moves the clip 502 distally relative to the cap 508 so that the clip 502 moves toward the deployed configuration. As described above, when the clip 502 is pushed distally off of the cap 508 toward the deployed configuration, the distal portion 548 of the deployment element 510 unwinds from the clip 502 so that the knot disengages the clip 502 and the clip 502 is released to clip the target tissue.

The repositioning element 512 may include, for example, a thread, strand, wire filament or other similar flexible longitudinal element. Rather than being releasably connected to the clip 502, however, the distal end 550 of the repositioning element 512 may be non-releasably affixed to a portion of the cap 508. According to one exemplary embodiment, the distal end 550 includes an enlarged end such as, for example, a knot, so that when the repositioning element 512 is passed through an opening extending through a wall of the cap 508, the knot 552 prevents the distal end 550 from passing therethrough. Thus, the knot of the repositioning element 512 engages the cap 508 along an exterior surface 542 of the cap 508 so that a remaining length of the repositioning element 512 extends through the opening, distally between an interior surface of the cap 508 and an exterior surface of the endoscope 504, distally between the biasing element 520 and the exterior surface of the endoscope 504 so that the repositioning element 512 is received within the distal opening of the channel of the endoscope 504 to extend proximally through the endoscope 504.

Thus, moving the repositioning element 512 proximally relative to the endoscope 504 moves the cap 508 distally relative to the endoscope 504 from the insertion configuration toward the review configuration. In this review configuration the biasing element 520 is maintained in a compressed configuration via tension along the repositioning element 512. If, however, it is determined during the review configuration that the clip 502 is not in the desired position relative to the target tissue, the tension along the repositioning element 512 may be released permitting the biasing element 520 to revert to its biased configuration which moves the cap 508 proximally relative to the endoscope 504, from the review configuration toward the insertion configuration.

Proximal ends of each of the deployment element 510 and the repositioning element 512 are, in this embodiment, connected to the actuator assembly 524 and coupled to a handle member of the endoscope 504. The actuator assembly 524 is substantially similar to the actuator assemblies described above, comprising a first actuator 561 for moving the clip 502 from the insertion configuration toward the review configuration and a second actuator 585 for moving the clip 502 from the review configuration toward the deployed configuration. The actuator assembly 524 may also include a housing 525 through which the proximal ends of the repositioning element 512 and the deployment element 510 extend to be connected to the first and second actuators 561, 585.

Figures 24, 25:
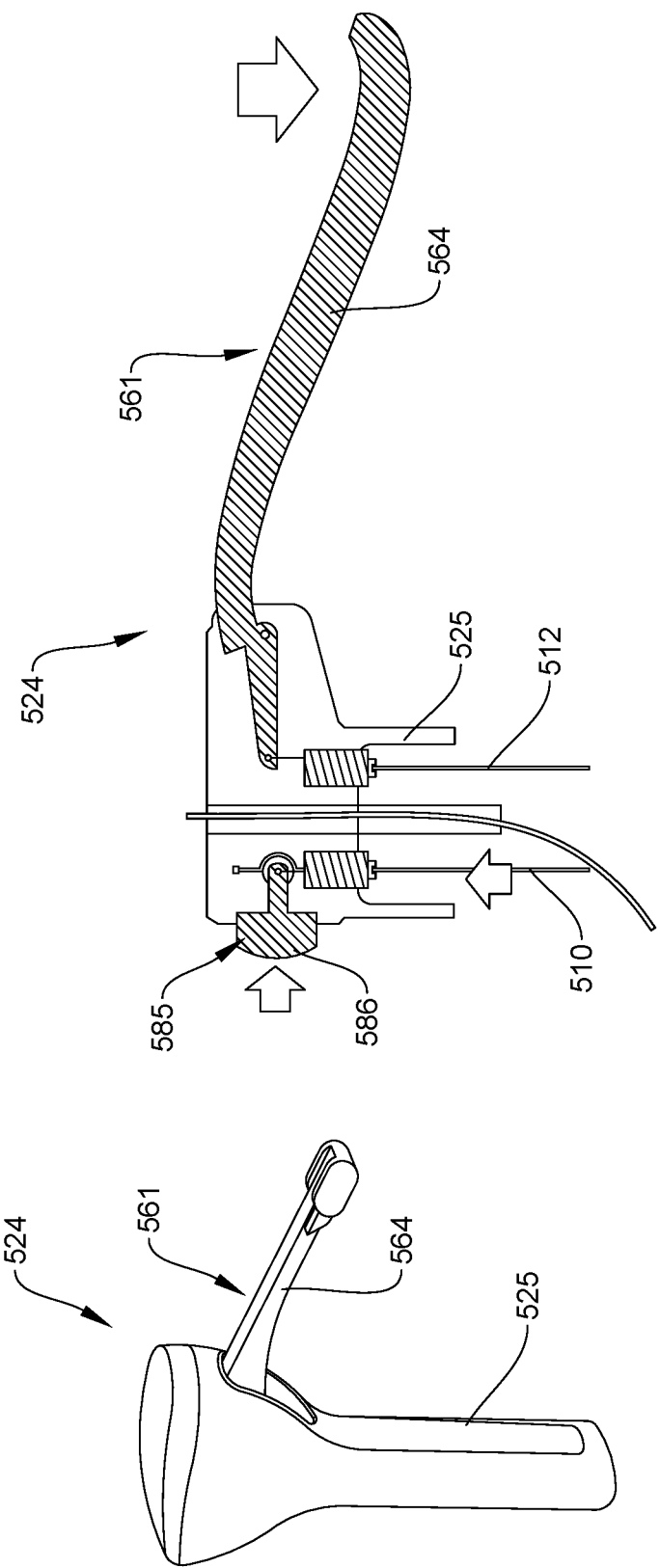
FIG. 24 shows a perspective view of an actuator assembly for controlling movement of a clip according to the system of FIG. 21.
FIG. 25 shows a cross-sectional side view of the actuator assembly of FIG. 24.

According to an exemplary embodiment, as shown in FIGS. 24-25, the actuator assembly 524 the first actuator 561 may include a lever 564 configured to control a movement of the repositioning element 512 relative to the endoscope 504 and the second actuator 585 may include a push button 586 for controlling a movement of the deployment element 510 relative to the endoscope 504. The lever 564 may be pivotally coupled to the housing 525 so that when the lever 564 is pressed toward the housing 525, the repositioning element 512 is drawn proximally through the endoscope 504. In particular, the proximal end of the repositioning element 512 is connected to the lever 564 such that, when the lever 564, is pressed, the repositioning element 512 is moved proximally relative to the endoscope 504, thereby moving the cap 508 distally relative to the endoscope from the insertion configuration toward the review configuration. The lever 564 should remain pressed to maintain the tension along the repositioning element 512 and keep the biasing element 520 compressed toward the review configuration.

If, during this review configuration, the operator determines that the clip 502 is in the desired position relative to the target tissue, the operator presses the push button 586 using, for example, his/her thumb. The push button 586 extends into the housing 525 and is connected to the proximal end of the deployment element 510 so that, when pressed, the deployment element 510 is drawn proximally relative to the endoscope 504 moving the clip 502 distally relative to the cap 508 until the clip 502 is moved distally off the cap 508. If, however, during the review configuration the operator determines that the clip 502 is not in the desired position relative to the target tissue, the operator releases the lever 564, releasing tension therealong and permitting the biasing element 520 to revert to its biased configuration. As the biasing element 520 reverts toward its biased configuration, the biasing element 520 pushes the cap 508 proximally along the endoscope 504 from the review configuration toward the insertion configuration so that, after releasing any tissue that had been drawn into the cap 508, the clip 502 may be repositioned, as necessary.

An exemplary method for clipping tissue using the clipping system 500 may be substantially similar to the method for clipping tissue using the system 100. Similarly to the system 100, the clip 502, mounted over the distal end 506 of the endoscope 504 via the cap 508 in the insertion configuration, as shown in FIG. 21, is inserted through a body lumen (e.g., of a gastrointestinal tract) to a target site within the body. As described above, the cap 508 is biased toward the insertion configuration via the biasing element 520.

Once the clip 502 is positioned over target tissue, the tissue is drawn into the cap 508 (e.g., via suction force may applied through a working channel of the endoscope 504) to extend between the jaws 514 of the clip 502. The clip 502 may then be moved from the insertion configuration toward the review configuration, as shown in FIG. 22, by moving the repositioning element 512 proximally relative to the endoscope 504 so that the cap 508 is moved distally which compresses the biasing element 520. In the review configuration, teeth 522 of this embodiment extend distally past the distal-most end 507 of the endoscope 504 so that a position of the teeth 522 relative to the target tissue is visible via the endoscope 504.

When the clip 502 is in the review configuration, the operator may determine whether the clip 502 is in the desired position relative to the target tissue. If the clip 502 is not in the desired position, a tension along the repositioning element 512 may be released so that the biasing element 520 may revert toward its biased configuration to move the cap 508 from the review configuration back toward the insertion configuration. Any tissue drawn into the cap 508 may then be released and, as the clip 502 is now in the insertion configuration, the endoscope 504 and the cap 5089 may be repositioned relative to the target tissue until the cap 508 and the clip 502 are in a desired position relative to the target tissue. Then the clip 502 may once again be moved toward the review configuration and this process may be repeated, as necessary, until the clip 502 is determined to be in the desired position relative to the target tissue.

Once it has been determined that the clip 502 is in the desired position, the clip 502 may be moved toward the deployed configuration by moving the deployment element 510 proximally relative to the endoscope 504 until the clip 502 has been pushed distally off of the cap 508, as shown in FIG. 23. As described above, when the clip 502 is pushed distally off the cap 508, the clip 502 is freed to revert toward its biased closed configuration so that the target tissue is gripped between the jaws 514.

In addition, since the deployment element 510 is no longer crimped between the clip 502 and the cap 508, the distal portion 548 of the deployment element 510 unwinds from the clip 502 so that the knot 546 disengages from and releases the clip 502 which remains clipped over the target tissue as the endoscope 504 along with the cap 508 are withdrawn from the body. It will be understood by those of skill in the art, that since the repositioning element 512 is connected to the cap 508 and is in no way connected to the clip 502, the repositioning element 512 need not release or disengage from the cap 508.

It will be apparent to those skilled in the art that various modifications may be made in the present disclosure, without departing from the scope of the disclosure. Furthermore, those skilled in the art will understand that the features of any of the various embodiments may be combined in any manner that is not inconsistent with the description and/or the functionality of the embodiments.

What is claimed is:

1. A clipping system for treating tissue, comprising:
   a cap configured to be mounted over a distal end of an endoscope, the cap extending longitudinally from a proximal end to a distal end and including a channel extending therethrough so that the cap may be located adjacent to target tissue within a living body;
   a clip configured to be mounted over the cap, the clip including first and second jaws movably connected to one via a hinge biased to draw the first and second jaws toward one another, the clip movable relative to the cap between: (a) an insertion configuration, in which the first and second jaws extend over the cap so that the first and second jaws are separated from one another to receive a target tissue therebetween and so that obstruction of an optical system of the endoscope on which the cap is mounted is minimized; (b) a review configuration, in which the clip is moved distally relative to the cap so that a portion of the clip extends distally until at least a portion of the clip extends into a field of view of the optical system on which the cap is mounted; and (c) a deployed configuration in which the clip is moved distally off of the cap so that the first and second jaws are drawn toward one another under the bias of the hinge to close and clip tissue received between the first and second jaws; and
   a control element extending from a distal end releasably coupled to the clip, through the channel of the cap and the endoscope to which it is connected, to a proximal end which, in use, remains outside the living body while the cap is adjacent to the target tissue, the control element being configured so that movement of the control element proximally through the cap moves the clip distally relative to the cap, the control element being configured so that movement of the control element proximally through the cap via a first distance moves the clip from the insertion configuration to the review configuration and movement of the control element proximally through the cap via a second distance moves the clip from the review configuration to the deployed configuration.

2. The system of claim 1, further comprising an actuator assembly connected to a proximal end of the control element, the actuator assembly including a first actuator configured so that, when actuated, the control element is moved proximally through the endoscope via the first distance to move the clip from the insertion configuration to the review configuration.

3. The system of claim 2, wherein the first actuator includes first and second longitudinal members pivotally coupled to one another so that when proximal portions of the first and second longitudinal members are drawn toward one another, distal portions of the first and second longitudinal members are correspondingly drawn toward one another.

4. The system of claim 2, wherein the actuator assembly further includes a second actuator configured so that, when actuated, the control element is moved proximally through the endoscope via the second distance to move the clip from the review configuration to the deployed configuration.

5. The system of claim 4, wherein the actuator assembly further comprises a moving element and a pulley mechanism, the control element being routed through the pulley mechanism to be connected to the moving element so that, when the first and second longitudinal members are drawn toward one another, the moving element is moved from a proximal position relative to a housing of the actuator assembly toward a distal position to pull the control element proximally through the endoscope such that the clip is moved from the insertion configuration toward the review configuration.

6. The system of claim 4, wherein the second actuator includes a push button including a tab extending into a housing of the actuator assembly such that when the clip is in the review configuration, the tab engages a portion of the control element so that pushing the push button exerts an additional tension along the control element which moves the clip from the review configuration toward the deployed configuration.

7. The system of claim 2, wherein the actuator assembly further comprises a biasing element biasing the first actuator toward the insertion configuration.

8. The system of claim 2, wherein the actuator assembly includes a locking mechanism for locking the clip toward the review configuration.

9. The system of claim 2, wherein the first actuator includes a handle portion configured to be gripped via an operator of the system and a lever movably coupled thereto, the proximal end of the control element connected to the lever so that, when the lever is pressed against the handle portion, the control element is moved proximally through the endoscope via the first distance to move the clip from the insertion configuration toward the review configuration.

10. The system of claim 9, further comprising:
    a biasing element extending between a distal end of the cap and a stop at a distal-most end of the endoscope on which the cap is mounted, the biasing element biasing the cap toward the insertion configuration, in which an entirety of the clip mounted over the cap is proximal of the distal-most end of the endoscope so that when the lever is released, the cap and the clip revert toward the insertion configuration.

11. The system of claim 2, wherein the first actuator includes a housing and a rotary handle rotatably couple thereto, the proximal end of the control element connected to a moving element threadedly coupled to a portion of the rotary handle so that a rotation of the rotary handle relative to the housing moves the control element proximally through the endoscope.

\* \* \* \* \*